United States Patent [19]
Greenspan et al.

[11] Patent Number: 5,939,321
[45] Date of Patent: Aug. 17, 1999

[54] MAMMALIAN TOLLOID-LIKE GENE AND PROTEIN

[75] Inventors: Daniel S. Greenspan; Kazuhiko Takahara; Guy G. Hoffman, all of Madison, Wis.

[73] Assignee: Wisconsin Alumni Research Foundatiion, Madison, Wis.

[21] Appl. No.: 08/866,650

[22] Filed: May 30, 1997

Related U.S. Application Data

[60] Provisional application No. 60/018,684, May 30, 1996.

[51] Int. Cl.$^6$ ..................................................... C12N 15/00
[52] U.S. Cl. ..................... 435/325; 435/69.1; 435/320.1; 435/455; 514/44; 424/93.21; 536/23.1
[58] Field of Search ..................................... 435/69.1, 325, 435/455, 320.1; 514/44; 424/93.21; 935/62, 52, 71; 536/23.1

[56] References Cited

PUBLICATIONS

Ronald Crystal, Science (1995) 270: 404–409.
Mastrangelo et al. (Seminars in Oncology, 1996, vol. 23, 1:4–21).
Ngo et al., in: The Protein Folding Problem and Tertiary Structure Prediction, 1994, Merz et al., (ed.), Birkhauser, Boston, MA, pp. 433 and 492–495.
Bond, Judith S., et al., "The astacin family of metalloendopeptidases," *Protein Science*, 4:1247–1261 (1995).
Johnson, George, "The Chicken With a Duck's Feet: It's All in the Biochemical Signal," *The New York Times Science* (May 21, 1996).
Kessler, Efrat, et al., "Bone Morphogenetic Protein–1: The Type I Procollagen C–Proteinase," *Science*, 271:360–362 (Jan. 19, 1996).
Takahara, Kazuhiko, et al., "Bone Morphogenetic Protein–1 and a Mammalian Tolloid Homologue (mTld) Are Encoded by Alternatively Spliced Transcripts Which Are Differentially Expressed in Some Tissues," *The Journal of Biological Chemistry*, 269(51):32572–32578 (1994).

*Primary Examiner*—Bruce R. Campell
*Assistant Examiner*—Dave Trong Nguyen
*Attorney, Agent, or Firm*—Quarles & Brady LLP

[57] ABSTRACT

A mammalian gene encoding a tolloid-like protein distinct from human or murine BMP-1/mTld is presented. The gene is similar in structure to members of the BMP-1 family of genes, but maps to a distinct location and encodes a distinct protein. The protein encoded by the gene can be used to screen putative therapeutic agents in an ongoing effort to inhibit activity of the BMP-1 family of genes to prevent scarring, fibrosis, and the like.

18 Claims, 3 Drawing Sheets

```
         Signal Peptide              Proregion
mTll   MGLQALSPRMLLWL.VVSGIVFSRVLWVCAGLDYDYTFDGNEEDKTEPIDYKDFCKAAVFWGDIALDDEDLNIFQIDRTIDLTQSPFGKLGHITGGFGDH  99
       I. I .I  II.I ::   :::  .. :..III:  . : .. :::..::  :..  I .::.:   IIIII:III. II::..  I I . : : .:I
mTld   MPGVARPPLPLLSLPLLLLLLLLPARRPAAGLG.RLHLRPGRGGRPGAPQLQRPLQGGCLPWDIALDEEDLRAFQVQQAAVLRQQTARRPSIKAAG....  95

GMPKKRGALYQLIERIRRIGSGLEQNNTMKGKAPPKLSEQSEKNRVPRAATSRTERIWPGGVIPYVIGGNFTGSQRAMFKQAMRHWEKHTCVTFTERSDE 199
              :I:I:...I  ......  :  .:: I .IIIIII.II:II:IIII:IIIIIIIIIIIII:I:IIIIIIIIIIIIIIII II.II
       .................NSSALGGQGTSGQPQRESRGRWRGRPRSRRAATSRPERVWPDGVIPFVIGGNFTGSQRAVFRQAMRHWEKHTCVTFLERTDE 178

ESYIVFTYRPFCKGCSYVGRRGNGPQAISIGKNCDKFGIVVHELGHVIGFWHEHTRPDRDNHVTIIRENIQPGQEYNFLKMEPGEVNSLGERYDFDSIMHY 299
       :IIIIIIIIIIIIIIIIIIII.IIIIIIIII.IIIIIIIIIIITITIIIIIIIIIIII.II..I:IIIIIIIIIIII..II:IIII IIIIIIIII
       DSYIVFTYRPFCKGCSYVGRRGGGPQAISIGKNCDKFGIVVHELGHVIGFWHEHTRPDRDRHVSIVRENIQPGQEYNFLKMEVQEVESLGETYDFDSIMHY 278
                                                             CUB 1
       ARNTFSRGMFLDTILPSRDDNGIRPAIGQRTRLSKGDIAQARKLYRCPACGETLQESSGNLSSPGFPNGYPSYTHCIWRVSVTPGEKIVLNFTTMDLYKS 399
       IIIIIII::IIIII:I. :  II::I.IIIIIIIIIIIIIIIII:IIIIIIII:I.II:III::IIII...  I::II:IIIIIII:IIII.IIII:I
       ARNTFSRGIFLDTIVPKYEVNGVKPSIGQRTRLSKGDIAQARKLYKCPACGETLQDSTGNFSSPEYPNGYSAHMHCVWRISVTPGEKIILNFTSMDLYRS 378
                                                        CUB 2
       SLCWYDYIEVRDGYWRKSPLLGRFCGDKVAGVLTSTDSRMWIEFRSSSNWVGKGFAAVYEAICGGEIRKNEGQIQSPNYPDDYRPMKECVWKIMVSEGYH 499
       .IIIII::IIIII:III  :  IIII::I:::..IIIII:I:IIIIIIIIII IIIIIII:::::I::I:IIIIIIIIII I I:I:I IIII:I
       RLCWYDYVEVRDGFWRKVWVRGRFCGGKLPEPIVSTDSRLWVEFRSSSNWVGKGFFAVYEAICGGDVKKDNGHIQSPNYPDDYRPSKVCIWRIQVSEGFH 478
                                                                                                  EGF 1
       VGLTFQAFEIERHDSCAYDHLEVRDGASENSPLIGRFCGYDKPEDIRSTSNTLWMKFVSDGTVNKAGFAANFFKEEDECAKPDRGGCEQRCLNTLGSYQC 599
       IIIIIIII.IIIIIIIIII.IIIIII II.I  IIII:III:.I:I:III. II:IIIII..:IIIIII.IIIII III..:I:IIIIIIIIIIIII.I
       VGLTFQSFEIERHDSCAYDYLEVRDGHSESSNLIGRYCGYENPDDIKSTSSRLWLKFVSDGSINKAGFAVNFFKEVDECSRPNRGGCEQRCLNTLGSYKC 578
                    CUB 3
       ACEPGYELGPDRRSCEAACGGLLTKLNGTITTPGWPKEYPPNKNCVWQVIAPSQYRISVKFEFFELEGNEVCKYDYVEIWSGPSSESKLHGKFCGADIPE 699
       .I:IIIII::II:I.IIIIII.IIIIIIIIIIIIIIII:IIIIIIII IIII:IIIIIII.:II .:IIIIIIIITI.: II
       SCDPGYELAPDKRRCEAACGGFLTKLNGSITSPGWPKEYPPNKNCIWQLVAPTQYRISLQFDFFETEGNDVCKYDFVEVRSGLTADSKLHGKFCGSEKPE 678
                                                         EGF 2                                      CUB 4
       VMTSHFNNMRIEFKSDNTVSKKGFKAHFFSDKDECSKDNGGCQHECVNTMGSYTCQCRNGFVLHENKHDCKEAECEQKIHSPSGLITSPNWPDKYPSRKE 799
       I:II::IIII:IIIIIIIIIIIIIIIIIIIIIIIIIIII::IIII:III.IIII.IIII:IIIIIII::I:I. I.II IIIIIIIIIIIIII:II
       VITSQYNNMRVEFKSDNTVSKKGFKAHFFSDKDECSKDNGGCQQICVNTFGSYECQCRSGFVLHDNKHDCKEAGCEHKVTSTSGTITSPNWPDKYPSKKE 778
                                                                                                    CUB 5
       CTWVISAIPGHRITLAFNEFEVEQHQECAYDHLEIFDGETEKSPILGRLCGSKIPDPLMATGNEMFIRFISDASVQRKGFQATHSTECGGRLKAESKPRD 899
       III.II..IIIII:.I.I I:::: :.ITIIIIIIII:III  ..I.I:III:IIII I:I:::IIII II::II.II.IIIIIIIII.IIIIIII.::I: I.:I
       CTWAISSTPGHRVKLTFVEMDIESQPECAYDHLEVFDGRDAKAPVLGRFCGSKKPEPVLATGNRMFLRFYSDNSVQRKGFQASHSTECGGQVRADVKTKD 878

LYSHAQFGDNNYPGQLDCEWLLVSERGSRLELSFQTFFEVEEEADCGYDYVEVFDGLSSKAVGLGRFCGSPPEEIYSIGDVALIHFHTDDTINKKGFYIR 999
       IIIIIIIIIIIII.:ITIII::I.I I   :II IIIIIIIIII.ITIIII:I:III..I.I. III:TIIIIIII:II II .I:.II.IIII.IIII.:I
       LYSHAQFGDNNYPGGVDCEWVIVAEEGYGVELVFQTFFEVEEETDCGYDYIELFDGYDSTAPRLGRYCGSPPEEVYSAGDSVLVKFHSDDTISKKGFHLR 978

YKSIRYPETMHAKN 1014
       I.I.:::.:I:I.:.
       YTSTKFQDTLHSRK 992
```

FIG 2

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 330 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide probe"

(xi) SEQUENCE DESCRIPTION: SEQ ID NO:1:

```
ACGTCCAGAC CGGAGCGGGT GTGGCCCGAT GGGGTCATCC CGTTTGTGAT TGGAGGGAAT      60

TTCACAGGCA GCCAGAGGGC AGTCTTCCGG CAGGCCATGA GACACTGGGA GAAGCATACC     120

TGTGTCACCT TCTTGGAGCG CACAGATGAG GACAGCTATA TTGTATTCAC CTACCGACCC     180
```

-continued

| | | |
|---|---|---|
| TGCGGGTGCT GCTCCTACGT GGGTCGCCGA GGTGGGGGCC CCCAGGCCAT CTCCATCGGC | 240 |
| AAGAACTGTG ACAAGTTTGG CATCGTGGTC CATGAGCTGG CCATGTCAT TGGCTTCTGG | 300 |
| CACGAGCACA CGCGGCCCGA CCGCGACCGC | 330 |

(2) INFORMATION FOR SEQ ID NO:2:

(i) SEQUENCE CHARACTERISTICS:
        (A) LENGTH: 4771 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 611..3652
        (D) OTHER INFORMATION: /product= "murine mTll protein"

(xi) SEQUENCE DESCRIPTION: SEQ ID NO:2:

```
CACACCCCTT TGCTCTCCGG GCAGTCGGGA GCTTCCCTAG CTTCGGCAGG CTTTTAAGGT    60

CTGGCGGCGT AGAAATGCCT ATCCCCCACC CCCTTCCTCG GTCTCCCCTT TCAGTTCAGA   120

TGTGCTGATG TGCAGACCGG ATTCATCTTC CCCGAGCAGC GGCGGTGGCA GCGGCGGGCG   180

CAGGCGGCTG CAGCTCGCTC TCGGCCGCGG GGTCCTGACA GCGGCGGGGG CGCGGCGCGG   240

GAGCCGGAGC TCCGGTGGCA GCTGAGCCCG CCGTGCGCCT CTCGCCGCGG CCGGTCGTGA   300

TCGCGGGAAG TTCGACCGCT GGAAGGACGA CCTAGACCGA GCCGGGTTGG CTGCGGCTGC   360

CCTGCGCCGA GCTCCTCACC TGCCTTCCGC CCACCCGCGG GCCCCCGGCC AAGTTCCCCA   420

GCATCCGGGG GAGACAGGGA GACATTTGCC CTCTCTAGCG TCCTGAAGAC ATCCGCATGT   480

CTCCGGACAC CTGAACATTC AGGTCTTTCC GAGGAGCTTC CCAGTCGGGA TAAGAACACT   540

GTCCCTAGAG CCCCGCATAT CCACGCGGCC CTCCGGGTCT GGTCCCCTCC TTTTCCTCTA   600

GGGGAGGAGG ATG GGT TTG CAA GCG CTC TCC CCG AGG ATG CTC CTG TGG     649
            Met Gly Leu Gln Ala Leu Ser Pro Arg Met Leu Leu Trp
              1               5                  10

TTG GTG GTC TCG GGT ATT GTT TTC TCC CGG GTG CTG TGG GTC TGC GCT     697
Leu Val Val Ser Gly Ile Val Phe Ser Arg Val Leu Trp Val Cys Ala
 15                  20                  25

GGC CTC GAT TAT GAT TAC ACT TTT GAT GGG AAC GAA GAG GAC AAA ACG     745
Gly Leu Asp Tyr Asp Tyr Thr Phe Asp Gly Asn Glu Glu Asp Lys Thr
 30                  35                  40                  45

GAG CCT ATA GAT TAC AAG GAC CCG TGC AAA GCT GCT GTG TTT TGG GGT     793
Glu Pro Ile Asp Tyr Lys Asp Pro Cys Lys Ala Ala Val Phe Trp Gly
                 50                  55                  60

GAC ATC GCC TTA GAT GAT GAA GAC TTA AAT ATC TTC CAA ATA GAC AGG     841
Asp Ile Ala Leu Asp Asp Glu Asp Leu Asn Ile Phe Gln Ile Asp Arg
             65                  70                  75

ACA ATT GAC CTG ACC CAG AGC CCC TTT GGA AAA CTT GGA CAT ATT ACA     889
Thr Ile Asp Leu Thr Gln Ser Pro Phe Gly Lys Leu Gly His Ile Thr
         80                  85                  90

GGT GGC TTT GGA GAC CAT GGC ATG CCA AAG AAG CGA GGG GCA CTC TAC     937
Gly Gly Phe Gly Asp His Gly Met Pro Lys Lys Arg Gly Ala Leu Tyr
     95                 100                 105

CAA CTT ATA GAG AGG ATC AGA AGA ATT GGC TCT GGC TTG GAG CAA AAT     985
Gln Leu Ile Glu Arg Ile Arg Arg Ile Gly Ser Gly Leu Glu Gln Asn
110                 115                 120                 125

AAC ACG ATG AAG GGA AAA GCA CCT CCA AAA TTG TCA GAG CAA AGT GAG    1033
Asn Thr Met Lys Gly Lys Ala Pro Pro Lys Leu Ser Glu Gln Ser Glu
                130                 135                 140
```

-continued

| | |
|---|---|
| AAA AAT CGA GTT CCC AGA GCT GCT ACC TCA AGA ACG GAA AGG ATA TGG<br>Lys Asn Arg Val Pro Arg Ala Ala Thr Ser Arg Thr Glu Arg Ile Trp<br>              145                    150                    155 | 1081 |
| CCT GGG GGT GTC ATT CCT TAT GTC ATA GGA GGA AAC TTT ACT GGC AGC<br>Pro Gly Gly Val Ile Pro Tyr Val Ile Gly Gly Asn Phe Thr Gly Ser<br>        160                    165                    170 | 1129 |
| CAG AGA GCC ATG TTC AAG CAG GCC ATG AGA CAC TGG GAA AAG CAC ACC<br>Gln Arg Ala Met Phe Lys Gln Ala Met Arg His Trp Glu Lys His Thr<br>175                    180                    185 | 1177 |
| TGT GTG ACG TTC ACT GAG AGA AGT GAT GAA GAA AGT TAT ATT GTG TTC<br>Cys Val Thr Phe Thr Glu Arg Ser Asp Glu Glu Ser Tyr Ile Val Phe<br>190                    195                    200                    205 | 1225 |
| ACC TAC AGG CCT TGT GGA TGC TGC TCC TAT GTT GGT CGG CGG GGA AAT<br>Thr Tyr Arg Pro Cys Gly Cys Cys Ser Tyr Val Gly Arg Arg Gly Asn<br>              210                    215                    220 | 1273 |
| GGC CCT CAG GCC ATC TCT ATT GGC AAG AAC TGT GAC AAG TTT GGA ATT<br>Gly Pro Gln Ala Ile Ser Ile Gly Lys Asn Cys Asp Lys Phe Gly Ile<br>              225                    230                    235 | 1321 |
| GTT GTT CAT GAA CTG GGC CAC GTG ATA GGC TTC TGG CAT GAA CAT ACC<br>Val Val His Glu Leu Gly His Val Ile Gly Phe Trp His Glu His Thr<br>        240                    245                    250 | 1369 |
| CGC CCA GAC CGA GAC AAC CAT GTC ACC ATC ATT AGA GAG AAC ATC CAG<br>Arg Pro Asp Arg Asp Asn His Val Thr Ile Ile Arg Glu Asn Ile Gln<br>255                    260                    265 | 1417 |
| CCA GGT CAA GAG TAC AAT TTT CTA AAG ATG GAG CCT GGA GAA GTG AAC<br>Pro Gly Gln Glu Tyr Asn Phe Leu Lys Met Glu Pro Gly Glu Val Asn<br>270                    275                    280                    285 | 1465 |
| TCT CTT GGG GAA AGA TAT GAT TTT GAC AGT ATC ATG CAC TAC GCC AGG<br>Ser Leu Gly Glu Arg Tyr Asp Phe Asp Ser Ile Met His Tyr Ala Arg<br>              290                    295                    300 | 1513 |
| AAC ACC TTC TCA AGA GGG ATG TTT TTA GAC ACA ATA CTC CCC TCC CGT<br>Asn Thr Phe Ser Arg Gly Met Phe Leu Asp Thr Ile Leu Pro Ser Arg<br>        305                    310                    315 | 1561 |
| GAT GAT AAT GGC ATT CGT CCT GCA ATT GGT CAA CGG ACC CGG TTA AGC<br>Asp Asp Asn Gly Ile Arg Pro Ala Ile Gly Gln Arg Thr Arg Leu Ser<br>320                    325                    330 | 1609 |
| AAA GGA GAC ATT GCA CAA GCA AGA AAG CTG TAT CGA TGC CCA GCA TGT<br>Lys Gly Asp Ile Ala Gln Ala Arg Lys Leu Tyr Arg Cys Pro Ala Cys<br>335                    340                    345 | 1657 |
| GGA GAA ACC CTG CAA GAA TCC AGT GGC AAC CTT TCT TCC CCA GGA TTC<br>Gly Glu Thr Leu Gln Glu Ser Ser Gly Asn Leu Ser Ser Pro Gly Phe<br>350                    355                    360                    365 | 1705 |
| CCA AAT GGC TAC CCT TCC TAC ACA CAC TGC ATC TGG AGA GTG TCT GTG<br>Pro Asn Gly Tyr Pro Ser Tyr Thr His Cys Ile Trp Arg Val Ser Val<br>              370                    375                    380 | 1753 |
| ACC CCG GGA GAA AAG ATT GTC TTG AAT TTT ACC ACA ATG GAC CTT TAC<br>Thr Pro Gly Glu Lys Ile Val Leu Asn Phe Thr Thr Met Asp Leu Tyr<br>        385                    390                    395 | 1801 |
| AAA AGT AGT TTG TGC TGG TAT GAT TAC ATT GAA GTA AGA GAT GGT TAC<br>Lys Ser Ser Leu Cys Trp Tyr Asp Tyr Ile Glu Val Arg Asp Gly Tyr<br>400                    405                    410 | 1849 |
| TGG AGG AAG TCA CCT CTC CTT GGT AGA TTC TGT GGG GAC AAA GTG GCT<br>Trp Arg Lys Ser Pro Leu Leu Gly Arg Phe Cys Gly Asp Lys Val Ala<br>415                    420                    425 | 1897 |
| GGA GTT CTT ACA TCT ACG GAC AGC AGA ATG TGG ATT GAG TTT CGT AGC<br>Gly Val Leu Thr Ser Thr Asp Ser Arg Met Trp Ile Glu Phe Arg Ser<br>430                    435                    440                    445 | 1945 |
| AGC AGT AAC TGG GTA GGA AAA GGG TTT GCA GCT GTC TAT GAA GCG ATT<br>Ser Ser Asn Trp Val Gly Lys Gly Phe Ala Ala Val Tyr Glu Ala Ile<br>              450                    455                    460 | 1993 |

-continued

| | | | | | | | | | | | | | | | |
|---|---|---|---|---|---|---|---|---|---|---|---|---|---|---|---|
| TGT | GGA | GGG | GAG | ATA | AGG | AAA | AAC | GAA | GGG | CAG | ATT | CAG | TCT | CCC | AAT | 2041 |
| Cys | Gly | Gly | Glu | Ile | Arg | Lys | Asn | Glu | Gly | Gln | Ile | Gln | Ser | Pro | Asn | |
| | | | | 465 | | | | 470 | | | | | 475 | | | |

| TAC | CCC | GAT | GAC | TAC | CGA | CCA | ATG | AAG | GAG | TGT | GTA | TGG | AAA | ATA | ATG | 2089 |
| Tyr | Pro | Asp | Asp | Tyr | Arg | Pro | Met | Lys | Glu | Cys | Val | Trp | Lys | Ile | Met | |
| | | | 480 | | | | | 485 | | | | | 490 | | | |

| GTG | TCC | GAG | GGC | TAC | CAT | GTT | GGA | CTG | ACC | TTT | CAG | GCC | TTT | GAG | ATC | 2137 |
| Val | Ser | Glu | Gly | Tyr | His | Val | Gly | Leu | Thr | Phe | Gln | Ala | Phe | Glu | Ile | |
| | 495 | | | | | 500 | | | | | 505 | | | | | |

| GAA | AGA | CAT | GAC | AGC | TGT | GCC | TAT | GAC | CAC | CTA | GAA | GTT | CGA | GAT | GGA | 2185 |
| Glu | Arg | His | Asp | Ser | Cys | Ala | Tyr | Asp | His | Leu | Glu | Val | Arg | Asp | Gly | |
| 510 | | | | | 515 | | | | | 520 | | | | | 525 | |

| GCC | AGT | GAG | AAC | AGC | CCT | TTG | ATA | GGA | CGG | TTC | TGT | GGT | TAT | GAC | AAA | 2233 |
| Ala | Ser | Glu | Asn | Ser | Pro | Leu | Ile | Gly | Arg | Phe | Cys | Gly | Tyr | Asp | Lys | |
| | | | | 530 | | | | | 535 | | | | | 540 | | |

| CCT | GAA | GAT | ATA | AGG | TCT | ACT | TCC | AAC | ACC | CTG | TGG | ATG | AAG | TTT | GTC | 2281 |
| Pro | Glu | Asp | Ile | Arg | Ser | Thr | Ser | Asn | Thr | Leu | Trp | Met | Lys | Phe | Val | |
| | | | 545 | | | | | 550 | | | | | 555 | | | |

| TCT | GAC | GGG | ACT | GTG | AAC | AAG | GCA | GGG | TTT | GCT | GCG | AAC | TTT | TTT | AAA | 2329 |
| Ser | Asp | Gly | Thr | Val | Asn | Lys | Ala | Gly | Phe | Ala | Ala | Asn | Phe | Phe | Lys | |
| | | 560 | | | | | 565 | | | | | 570 | | | | |

| GAG | GAA | GAT | GAG | TGT | GCC | AAA | CCT | GAC | CGA | GGA | GGC | TGT | GAA | CAG | AGG | 2377 |
| Glu | Glu | Asp | Glu | Cys | Ala | Lys | Pro | Asp | Arg | Gly | Gly | Cys | Glu | Gln | Arg | |
| | 575 | | | | | 580 | | | | | 585 | | | | | |

| TGT | CTT | AAC | ACA | CTA | GGC | AGC | TAC | CAG | TGT | GCC | TGT | GAG | CCT | GGC | TAT | 2425 |
| Cys | Leu | Asn | Thr | Leu | Gly | Ser | Tyr | Gln | Cys | Ala | Cys | Glu | Pro | Gly | Tyr | |
| 590 | | | | | 595 | | | | | 600 | | | | | 605 | |

| GAA | CTG | GGG | CCA | GAC | AGA | AGA | AGC | TGT | GAA | GCT | GCT | TGC | GGA | GGA | CTT | 2473 |
| Glu | Leu | Gly | Pro | Asp | Arg | Arg | Ser | Cys | Glu | Ala | Ala | Cys | Gly | Gly | Leu | |
| | | | | 610 | | | | | 615 | | | | | 620 | | |

| CTG | ACG | AAG | CTC | AAT | GGC | ACC | ATA | ACC | ACC | CCC | GGC | TGG | CCC | AAA | GAG | 2521 |
| Leu | Thr | Lys | Leu | Asn | Gly | Thr | Ile | Thr | Thr | Pro | Gly | Trp | Pro | Lys | Glu | |
| | | | 625 | | | | | 630 | | | | | 635 | | | |

| TAC | CCT | CCA | AAC | AAA | AAC | TGT | GTG | TGG | CAA | GTG | ATC | GCG | CCA | AGC | CAG | 2569 |
| Tyr | Pro | Pro | Asn | Lys | Asn | Cys | Val | Trp | Gln | Val | Ile | Ala | Pro | Ser | Gln | |
| | | | 640 | | | | | 645 | | | | | 650 | | | |

| TAC | AGA | ATC | TCT | GTG | AAG | TTT | GAG | TTT | TTT | GAA | TTG | GAA | GGC | AAT | GAA | 2617 |
| Tyr | Arg | Ile | Ser | Val | Lys | Phe | Glu | Phe | Phe | Glu | Leu | Glu | Gly | Asn | Glu | |
| | 655 | | | | | 660 | | | | | 665 | | | | | |

| GTT | TGC | AAA | TAC | GAT | TAC | GTG | GAG | ATC | TGG | AGC | GGC | CCT | TCC | TCT | GAG | 2665 |
| Val | Cys | Lys | Tyr | Asp | Tyr | Val | Glu | Ile | Trp | Ser | Gly | Pro | Ser | Ser | Glu | |
| 670 | | | | | 675 | | | | | 680 | | | | | 685 | |

| TCT | AAA | CTG | CAT | GGC | AAG | TTC | TGT | GGC | GCT | GAC | ATA | CCT | GAA | GTG | ATG | 2713 |
| Ser | Lys | Leu | His | Gly | Lys | Phe | Cys | Gly | Ala | Asp | Ile | Pro | Glu | Val | Met | |
| | | | | 690 | | | | | 695 | | | | | 700 | | |

| ACT | TCC | CAT | TTC | AAC | AAC | ATG | AGG | ATT | GAA | TTC | AAG | TCA | GAC | AAC | ACT | 2761 |
| Thr | Ser | His | Phe | Asn | Asn | Met | Arg | Ile | Glu | Phe | Lys | Ser | Asp | Asn | Thr | |
| | | | 705 | | | | | 710 | | | | | 715 | | | |

| GTA | TCC | AAG | AAG | GGC | TTC | AAA | GCA | CAT | TTT | TTC | TCA | GAT | AAG | GAT | GAG | 2809 |
| Val | Ser | Lys | Lys | Gly | Phe | Lys | Ala | His | Phe | Phe | Ser | Asp | Lys | Asp | Glu | |
| | | 720 | | | | | 725 | | | | | 730 | | | | |

| TGT | TCA | AAG | GAT | AAT | GGT | GGC | TGT | CAG | CAT | GAG | TGT | GTC | AAC | ACG | ATG | 2857 |
| Cys | Ser | Lys | Asp | Asn | Gly | Gly | Cys | Gln | His | Glu | Cys | Val | Asn | Thr | Met | |
| | 735 | | | | | 740 | | | | | 745 | | | | | |

| GGA | AGT | TAC | ACG | TGT | CAG | TGC | CGG | AAT | GGA | TTC | GTG | TTG | CAT | GAG | AAC | 2905 |
| Gly | Ser | Tyr | Thr | Cys | Gln | Cys | Arg | Asn | Gly | Phe | Val | Leu | His | Glu | Asn | |
| 750 | | | | | 755 | | | | | 760 | | | | | 765 | |

| AAG | CAT | GAT | TGC | AAG | GAA | GCC | GAG | TGT | GAA | CAG | AAG | ATA | CAC | AGC | CCA | 2953 |
| Lys | His | Asp | Cys | Lys | Glu | Ala | Glu | Cys | Glu | Gln | Lys | Ile | His | Ser | Pro | |
| | | | | 770 | | | | | 775 | | | | | 780 | | |

```
AGT GGT CTC ATC ACC AGT CCC AAC TGG CCA GAC AAG TAT CCA AGC AGG    3001
Ser Gly Leu Ile Thr Ser Pro Asn Trp Pro Asp Lys Tyr Pro Ser Arg
            785                 790                 795

AAA GAG TGC ACG TGG GTG ATC AGT GCC ATT CCT GGC CAC CGC ATC ACA    3049
Lys Glu Cys Thr Trp Val Ile Ser Ala Ile Pro Gly His Arg Ile Thr
            800                 805                 810

TTA GCC TTC AAT GAG TTT GAG GTT GAA CAA CAT CAA GAA TGT GCT TAT    3097
Leu Ala Phe Asn Glu Phe Glu Val Glu Gln His Gln Glu Cys Ala Tyr
            815                 820                 825

GAT CAC TTG GAA ATT TTT GAT GGA GAA ACG GAG AAG TCA CCA ATA CTT    3145
Asp His Leu Glu Ile Phe Asp Gly Glu Thr Glu Lys Ser Pro Ile Leu
830                 835                 840                 845

GGC CGA CTA TGT GGC AGC AAG ATA CCA GAT CCC CTC ATG GCT ACT GGG    3193
Gly Arg Leu Cys Gly Ser Lys Ile Pro Asp Pro Leu Met Ala Thr Gly
                850                 855                 860

AAT GAA ATG TTT ATT CGG TTT ATT TCT GAT GCC TCT GTT CAA AGA AAA    3241
Asn Glu Met Phe Ile Arg Phe Ile Ser Asp Ala Ser Val Gln Arg Lys
                865                 870                 875

GGC TTT CAA GCT ACA CAT TCC ACA GAG TGT GGT GGT CGA TTG AAA GCA    3289
Gly Phe Gln Ala Thr His Ser Thr Glu Cys Gly Gly Arg Leu Lys Ala
                880                 885                 890

GAG TCA AAG CCT AGA GAC CTG TAC TCC CAT GCT CAG TTT GGT GAT AAT    3337
Glu Ser Lys Pro Arg Asp Leu Tyr Ser His Ala Gln Phe Gly Asp Asn
            895                 900                 905

AAC TAC CCA GGA CAA CTG GAC TGT GAA TGG TTG TTG GTG TCA GAA CGA    3385
Asn Tyr Pro Gly Gln Leu Asp Cys Glu Trp Leu Leu Val Ser Glu Arg
910                 915                 920                 925

GGA TCT CGA CTT GAA TTG TCC TTC CAG ACA TTC GAA GTA GAA GAA GAA    3433
Gly Ser Arg Leu Glu Leu Ser Phe Gln Thr Phe Glu Val Glu Glu Glu
                930                 935                 940

GCT GAC TGT GGC TAT GAC TAT GTT GAA GTC TTT GAT GGT CTC AGT TCA    3481
Ala Asp Cys Gly Tyr Asp Tyr Val Glu Val Phe Asp Gly Leu Ser Ser
                945                 950                 955

AAA GCT GTG GGT CTT GGT AGA TTC TGT GGG TCA GGG CCA CCA GAA GAA    3529
Lys Ala Val Gly Leu Gly Arg Phe Cys Gly Ser Gly Pro Pro Glu Glu
                960                 965                 970

ATC TAT TCA ATT GGA GAT GTG GCT TTG ATT CAT TTC CAC ACA GAT GAC    3577
Ile Tyr Ser Ile Gly Asp Val Ala Leu Ile His Phe His Thr Asp Asp
            975                 980                 985

ACT ATC AAC AAG AAA GGA TTT TAT ATA AGA TAT AAA AGT ATA AGA TAC    3625
Thr Ile Asn Lys Lys Gly Phe Tyr Ile Arg Tyr Lys Ser Ile Arg Tyr
990                 995                 1000                1005

CCG GAA ACG ATG CAT GCC AAG AAC TAA TGCCGACCCT CCCTCAGAAC          3672
Pro Glu Thr Met His Ala Lys Asn *
            1010

AGAAAGGAAT GTGCATATGG AAAGAAGACA TTTTTAAAAT AGACAATATT AATACAATTG  3732

TTTTATATAA TGAATTTGAG CAAAAGAAAC CTGCAAGATT AGAGTTATCT CTGAAGTGAA  3792

AGAGAACTTT CCAGAAAACC TGATTGGCAT TGCAAGGATG TTTGAAAGTC ATGCTTGTTC  3852

AAGGAAGATT AACAGCTTGA AATAGATGCT TCACATTTTG GACAGTTCAT TTAATGAGCT  3912

GTGATTCTCT GGAGTGATTT CTTGACTACT TTTCCAAGAT CTGGGGACGT AGAAATGATG  3972

GGACGGATCA TAGCTTGGAA ACCCACTTCT TGGGTCTTAG CATGTTTGCT TAGACTCTGT  4032

AGGTCAGACA CAGTGTAAAC CAAATTCATG TAAGGTGATG TGGAATAGTG GTCTTTGGAA  4092

GGTGGTTCAT CATTTAAATG TAGGTTTGTG CTTGTGTGTA TGTTCACATA TGCAAGTGTG  4152

TGTGTGTGTG TGTGTGTGTG TGTGTGTGTG TGTGTGCGTG TGTGTGTGTG TGCGTGTGTG  4212

TGTGTGTGCA TGTGTGTGCA TGTGTGTTTG GAAACTGGAA TATTTCATCT TCATTATTTT  4272
```

```
CAAATGCAGG CCAGCTTAAC CTGTTCACAC AAATGATTTT GTGACCACTT CATTGTATCT      4332

GTATCTTGAG AAGTTTGAAA TATCTATAGT GTCTACAATG CAGTTAATCC CTAGATATCG      4392

GATAATACCC AGTTCACTAG TAAACTCATT TCTCTCTGGG GAAGTGCTGA ATAGTCTCCA      4452

AATTCAAGAA ACTCACCATG TCTTATAAAC CTTTAAGATA AAATTCCAAC GAGGTGTGTG      4512

CAGCCATCTT CCAAATGACT GCCTGGATGT TTCTTAGTCC AGTTACTACT GCTGCTGCTA      4572

TTGGTCTTTC TTTTATTGTT AATGTGTTGA TATGTTGTTA TTATTATGGT TATTATTATT      4632

GATGTTGTTA CTATATTTAA AAATGATGAG ATGAAGTGGA AGTAGAGTTT GGGAGAAATG      4692

AAATCTCTCT TTTTTGTTCT CTTCTTGAAA TTCAGTTTCA AAAAATACAA TATTGGGTGG      4752

CAAAAAAAAA AAAAAAAA                                                    4771
```

(2) INFORMATION FOR SEQ ID NO:3:

(i) SEQUENCE CHARACTERISTICS:
        (A) LENGTH: 1013 amino acids
        (B) TYPE: amino acid
        (D) TOPOLOGY: linear (ii) MOLECULE TYPE: protein (xi) SEQUENCE DESCRIPTION: SEQ ID NO:3:

```
Met Gly Leu Gln Ala Leu Ser Pro Arg Met Leu Leu Trp Leu Val Val
 1               5                  10                  15

Ser Gly Ile Val Phe Ser Arg Val Leu Trp Val Cys Ala Gly Leu Asp
             20                  25                  30

Tyr Asp Tyr Thr Phe Asp Gly Asn Glu Glu Asp Lys Thr Glu Pro Ile
         35                  40                  45

Asp Tyr Lys Asp Pro Cys Lys Ala Ala Val Phe Trp Gly Asp Ile Ala
 50                  55                  60

Leu Asp Asp Glu Asp Leu Asn Ile Phe Gln Ile Asp Arg Thr Ile Asp
 65                  70                  75                  80

Leu Thr Gln Ser Pro Phe Gly Lys Leu Gly His Ile Thr Gly Gly Phe
             85                  90                  95

Gly Asp His Gly Met Pro Lys Lys Arg Gly Ala Leu Tyr Gln Leu Ile
            100                 105                 110

Glu Arg Ile Arg Arg Ile Gly Ser Gly Leu Glu Gln Asn Asn Thr Met
        115                 120                 125

Lys Gly Lys Ala Pro Pro Lys Leu Ser Glu Gln Ser Glu Lys Asn Arg
130                 135                 140

Val Pro Arg Ala Ala Thr Ser Arg Thr Glu Arg Ile Trp Pro Gly Gly
145                 150                 155                 160

Val Ile Pro Tyr Val Ile Gly Gly Asn Phe Thr Gly Ser Gln Arg Ala
                165                 170                 175

Met Phe Lys Gln Ala Met Arg His Trp Glu Lys His Thr Cys Val Thr
            180                 185                 190

Phe Thr Glu Arg Ser Asp Glu Glu Ser Tyr Ile Val Phe Thr Tyr Arg
        195                 200                 205

Pro Cys Gly Cys Cys Ser Tyr Val Gly Arg Arg Gly Asn Gly Pro Gln
    210                 215                 220

Ala Ile Ser Ile Gly Lys Asn Cys Asp Lys Phe Gly Ile Val Val His
225                 230                 235                 240

Glu Leu Gly His Val Ile Gly Phe Trp His Glu His Thr Arg Pro Asp
                245                 250                 255

Arg Asp Asn His Val Thr Ile Ile Arg Glu Asn Ile Gln Pro Gly Gln
            260                 265                 270
```

```
Glu Tyr Asn Phe Leu Lys Met Glu Pro Gly Glu Val Asn Ser Leu Gly
        275                 280                 285

Glu Arg Tyr Asp Phe Asp Ser Ile Met His Tyr Ala Arg Asn Thr Phe
        290                 295                 300

Ser Arg Gly Met Phe Leu Asp Thr Ile Leu Pro Ser Arg Asp Asp Asn
305                 310                 315                 320

Gly Ile Arg Pro Ala Ile Gly Gln Arg Thr Arg Leu Ser Lys Gly Asp
                325                 330                 335

Ile Ala Gln Ala Arg Lys Leu Tyr Arg Cys Pro Ala Cys Gly Glu Thr
                340                 345                 350

Leu Gln Glu Ser Ser Gly Asn Leu Ser Ser Pro Gly Phe Pro Asn Gly
        355                 360                 365

Tyr Pro Ser Tyr Thr His Cys Ile Trp Arg Val Ser Val Thr Pro Gly
        370                 375                 380

Glu Lys Ile Val Leu Asn Phe Thr Thr Met Asp Leu Tyr Lys Ser Ser
385                 390                 395                 400

Leu Cys Trp Tyr Asp Tyr Ile Glu Val Arg Asp Gly Tyr Trp Arg Lys
                405                 410                 415

Ser Pro Leu Leu Gly Arg Phe Cys Gly Asp Lys Val Ala Gly Val Leu
                420                 425                 430

Thr Ser Thr Asp Ser Arg Met Trp Ile Glu Phe Arg Ser Ser Ser Asn
        435                 440                 445

Trp Val Gly Lys Gly Phe Ala Ala Val Tyr Glu Ala Ile Cys Gly Gly
        450                 455                 460

Glu Ile Arg Lys Asn Glu Gly Gln Ile Gln Ser Pro Asn Tyr Pro Asp
465                 470                 475                 480

Asp Tyr Arg Pro Met Lys Glu Cys Val Trp Lys Ile Met Val Ser Glu
                485                 490                 495

Gly Tyr His Val Gly Leu Thr Phe Gln Ala Phe Glu Ile Glu Arg His
                500                 505                 510

Asp Ser Cys Ala Tyr Asp His Leu Glu Val Arg Asp Gly Ala Ser Glu
        515                 520                 525

Asn Ser Pro Leu Ile Gly Arg Phe Cys Gly Tyr Asp Lys Pro Glu Asp
        530                 535                 540

Ile Arg Ser Thr Ser Asn Thr Leu Trp Met Lys Phe Val Ser Asp Gly
545                 550                 555                 560

Thr Val Asn Lys Ala Gly Phe Ala Ala Asn Phe Phe Lys Glu Glu Asp
                565                 570                 575

Glu Cys Ala Lys Pro Asp Arg Gly Gly Cys Glu Gln Arg Cys Leu Asn
                580                 585                 590

Thr Leu Gly Ser Tyr Gln Cys Ala Cys Glu Pro Gly Tyr Glu Leu Gly
        595                 600                 605

Pro Asp Arg Arg Ser Cys Glu Ala Ala Cys Gly Gly Leu Leu Thr Lys
        610                 615                 620

Leu Asn Gly Thr Ile Thr Thr Pro Gly Trp Pro Lys Glu Tyr Pro Pro
625                 630                 635                 640

Asn Lys Asn Cys Val Trp Gln Val Ile Ala Pro Ser Gln Tyr Arg Ile
                645                 650                 655

Ser Val Lys Phe Glu Phe Phe Glu Leu Glu Gly Asn Glu Val Cys Lys
                660                 665                 670

Tyr Asp Tyr Val Glu Ile Trp Ser Gly Pro Ser Ser Glu Ser Lys Leu
        675                 680                 685

His Gly Lys Phe Cys Gly Ala Asp Ile Pro Glu Val Met Thr Ser His
```

```
                        690                 695                 700
Phe Asn Asn Met Arg Ile Glu Phe Lys Ser Asp Asn Thr Val Ser Lys
705                 710                 715                 720

Lys Gly Phe Lys Ala His Phe Phe Ser Asp Lys Asp Glu Cys Ser Lys
                725                 730                 735

Asp Asn Gly Gly Cys Gln His Glu Cys Val Asn Thr Met Gly Ser Tyr
            740                 745                 750

Thr Cys Gln Cys Arg Asn Gly Phe Val Leu His Glu Asn Lys His Asp
        755                 760                 765

Cys Lys Glu Ala Glu Cys Glu Gln Lys Ile His Ser Pro Ser Gly Leu
770                 775                 780

Ile Thr Ser Pro Asn Trp Pro Asp Lys Tyr Pro Ser Arg Lys Glu Cys
785                 790                 795                 800

Thr Trp Val Ile Ser Ala Ile Pro Gly His Arg Ile Thr Leu Ala Phe
                805                 810                 815

Asn Glu Phe Glu Val Glu Gln His Gln Glu Cys Ala Tyr Asp His Leu
            820                 825                 830

Glu Ile Phe Asp Gly Glu Thr Glu Lys Ser Pro Ile Leu Gly Arg Leu
        835                 840                 845

Cys Gly Ser Lys Ile Pro Asp Pro Leu Met Ala Thr Gly Asn Glu Met
850                 855                 860

Phe Ile Arg Phe Ile Ser Asp Ala Ser Val Gln Arg Lys Gly Phe Gln
865                 870                 875                 880

Ala Thr His Ser Thr Glu Cys Gly Gly Arg Leu Lys Ala Glu Ser Lys
                885                 890                 895

Pro Arg Asp Leu Tyr Ser His Ala Gln Phe Gly Asp Asn Asn Tyr Pro
            900                 905                 910

Gly Gln Leu Asp Cys Glu Trp Leu Leu Val Ser Glu Arg Gly Ser Arg
        915                 920                 925

Leu Glu Leu Ser Phe Gln Thr Phe Glu Val Glu Glu Ala Asp Cys
930                 935                 940

Gly Tyr Asp Tyr Val Glu Val Phe Asp Gly Leu Ser Ser Lys Ala Val
945                 950                 955                 960

Gly Leu Gly Arg Phe Cys Gly Ser Gly Pro Pro Glu Glu Ile Tyr Ser
                965                 970                 975

Ile Gly Asp Val Ala Leu Ile His Phe His Thr Asp Asp Thr Ile Asn
            980                 985                 990

Lys Lys Gly Phe Tyr Ile Arg Tyr Lys Ser Ile Arg Tyr Pro Glu Thr
        995                 1000                1005

Met His Ala Lys Asn
        1010

(2) INFORMATION FOR SEQ ID NO:4:

(i) SEQUENCE CHARACTERISTICS:
        (A) LENGTH: 3919 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: CDS
        (B) LOCATION: 648..3689
        (D) OTHER INFORMATION: /product= "human mT11 protein"
```

(xi) SEQUENCE DESCRIPTION: SEQ ID NO:4:

```
CTCACACTTT TGCTCTCTTG CAGTCAGTTG CTTTGCTGGC TTCTGCAGGC TTTTAAGGTC        60

TCGCGGCGTA GAAATGCCTG GCCCCCACCC CCTTCCTCGG TCTCCCCTTT CAATTCAGAT       120

GTGCTGATGT GCAGACCGGA TTCATCTTCT CGGAGCTGCG GCGGCGGCTT TGGGCTCAGG       180

CGGCGGCGGC TCGCGCTCGG CCGCGGAGTC CTGGCAGCAG CGGGGACGCG GCGCGGGAGT       240

CCGAGCTCTG GTGGCAGCTG AGCCCGCGGG GCGCCGCTCG CCGAGCCGCG GCCGCGGGAA       300

GTTCGGCAGC CAGAAGGACG ACCTGGCAGG CTGCGAGCGC CAGCGCCGCC AGAGCCGAGT       360

TTGCCTGCGC CCTCCCCGCC TCCGAGTGCA GAGTTCCTTA CCTGCCCTCC GCCCACCCGT       420

GGGCCCCTAG CCAACTTCTC CCTGCGACTG GGGGTAACAG GCAGTGCTTG CCCTCTCTAC       480

TGTCCCGGCG GCATCCACAT GTTTCCGGAC ACCTGAGCAC CCCGGTCCCG CCGAGGAGCC       540

TCCGGGTGGG GAGAAGAGCA CCGGTGCCCC TAGCCCCGCA CATCAGCGCG GACCGCGGCT       600

GCCTAACCTC TGGGTCCCGT CCCCTCCTTT TCCTCCGGGG GAGGAGG ATG GGG TTG         656
                                                   Met Gly Leu
                                                   1015
```

GGA ACG CTT TCC CCG AGG ATG CTC GTG TGG CTG GTG GCC TCG GGG ATT        704
Gly Thr Leu Ser Pro Arg Met Leu Val Trp Leu Val Ala Ser Gly Ile
        1020            1025            1030

GTT TTC TAC GGG GAG CTA TGG GTC TGC GCT GGC CTC GAT TAT GAT TAC        752
Val Phe Tyr Gly Glu Leu Trp Val Cys Ala Gly Leu Asp Tyr Asp Tyr
        1035            1040            1045

ACT TTT GAT GGG AAC GAA GAG GAT AAA ACA GAG ACT ATA GAT TAC AAG        800
Thr Phe Asp Gly Asn Glu Glu Asp Lys Thr Glu Thr Ile Asp Tyr Lys
1050            1055            1060            1065

GAC CCG TGT AAA GCC GCT GTA TTT TGG GGC GAT ATT GCC TTA GAT GAT        848
Asp Pro Cys Lys Ala Ala Val Phe Trp Gly Asp Ile Ala Leu Asp Asp
            1070            1075            1080

GAA GAC TTA AAT ATC TTT CAA ATA GAT AGG ACA ATT GAC CTT ACG CAG        896
Glu Asp Leu Asn Ile Phe Gln Ile Asp Arg Thr Ile Asp Leu Thr Gln
            1085            1090            1095

AAC CCC TTT GGA AAC CTT GGA CAT ACC ACA GGT GGA CTT GGA GAC CAT        944
Asn Pro Phe Gly Asn Leu Gly His Thr Thr Gly Gly Leu Gly Asp His
            1100            1105            1110

GCT ATG TCA AAG AAG CGA GGG GCC CTC TAC CAA CTT ATA GAC AGG ATA        992
Ala Met Ser Lys Lys Arg Gly Ala Leu Tyr Gln Leu Ile Asp Arg Ile
        1115            1120            1125

AGA AGA ATT GGC TTT GGC TTG GAG CAA AAC AAC ACA GTT AAG GGA AAA       1040
Arg Arg Ile Gly Phe Gly Leu Glu Gln Asn Asn Thr Val Lys Gly Lys
1130            1135            1140            1145

GTA CCT CTA CAA TTC TCA GGG CAA AAT GAG AAA AAT CGA GTT CCC AGA       1088
Val Pro Leu Gln Phe Ser Gly Gln Asn Glu Lys Asn Arg Val Pro Arg
            1150            1155            1160

GCC GCT ACA TCA AGA ACG GAA AGA ATA TGG CCT GGA GGC GTT ATT CCT       1136
Ala Ala Thr Ser Arg Thr Glu Arg Ile Trp Pro Gly Gly Val Ile Pro
            1165            1170            1175

TAT GTT ATA GGA GGA AAC TTC ACT GGC AGC CAG AGA GCC ATG TTC AAG       1184
Tyr Val Ile Gly Gly Asn Phe Thr Gly Ser Gln Arg Ala Met Phe Lys
        1180            1185            1190

CAG GCC ATG AGG CAC TGG GAA AAG CAC ACA TGT GTG ACT TTC ATA GAA       1232
Gln Ala Met Arg His Trp Glu Lys His Thr Cys Val Thr Phe Ile Glu
        1195            1200            1205

AGA AGT GAT GAA GAG AGT TAC ATT GTA TTC ACC TAT AGG CCT TGT GGA       1280
Arg Ser Asp Glu Glu Ser Tyr Ile Val Phe Thr Tyr Arg Pro Cys Gly
1210            1215            1220            1225

TGC TGC TCC TAT GTA GGT CGG CGA GGA AAT GGA CCT CAG GCA ATC TCT       1328

```
Cys Cys Ser Tyr Val Gly Arg Arg Gly Asn Gly Pro Gln Ala Ile Ser
            1230                1235                1240

ATC GGC AAG AAC TGT GAT AAA TTT GGG ATT GTT GTT CAT GAA TTG GGT       1376
Ile Gly Lys Asn Cys Asp Lys Phe Gly Ile Val Val His Glu Leu Gly
            1245                1250                1255

CAT GTG ATA GGC TTT TGG CAT GAA CAC ACA AGA CCA GAT CGA GAT AAC       1424
His Val Ile Gly Phe Trp His Glu His Thr Arg Pro Asp Arg Asp Asn
            1260                1265                1270

CAC GTA ACT ATC ATA AGA GAA AAC ATC CAG CCA GGT CAA GAG TAC AAT       1472
His Val Thr Ile Ile Arg Glu Asn Ile Gln Pro Gly Gln Glu Tyr Asn
            1275                1280                1285

TTT CTG AAG ATG GAG CCT GGA GAA GTA AAC TCA CTT GGA GAA AGA TAT       1520
Phe Leu Lys Met Glu Pro Gly Glu Val Asn Ser Leu Gly Glu Arg Tyr
1290            1295                1300                1305

GAT TTC GAC AGT ATC ATG CAC TAT GCC AGG AAC ACC TTC TCA AGG GGG       1568
Asp Phe Asp Ser Ile Met His Tyr Ala Arg Asn Thr Phe Ser Arg Gly
            1310                1315                1320

ATG TTT CTG GAT ACC ATT CTC CCC TCC CGT GAT GAT AAT GGC ATA CGT       1616
Met Phe Leu Asp Thr Ile Leu Pro Ser Arg Asp Asp Asn Gly Ile Arg
            1325                1330                1335

CCT GCA ATT GGT CAG CGA ACC CGT CTA AGC AAA GGA GAT ATC GCA CAG       1664
Pro Ala Ile Gly Gln Arg Thr Arg Leu Ser Lys Gly Asp Ile Ala Gln
            1340                1345                1350

GCA AGA AAG CTG TAT AGA TGT CCA GCA TGT GGA GAA ACT CTA CAA GAA       1712
Ala Arg Lys Leu Tyr Arg Cys Pro Ala Cys Gly Glu Thr Leu Gln Glu
            1355                1360                1365

TCC AAT GGC AAC CTT TCC TCT CCA GGA TTT CCC AAT GGC TAC CCT TCT       1760
Ser Asn Gly Asn Leu Ser Ser Pro Gly Phe Pro Asn Gly Tyr Pro Ser
1370            1375                1380                1385

TAC ACA CAC TGC ATC TGG AGA GTT TCT GTG ACC CCA GGG GAG AAG ATT       1808
Tyr Thr His Cys Ile Trp Arg Val Ser Val Thr Pro Gly Glu Lys Ile
            1390                1395                1400

GTT TTA AAT TTT ACA ACG ATG GAT CTA TAC AAG AGT AGT TTG TGC TGG       1856
Val Leu Asn Phe Thr Thr Met Asp Leu Tyr Lys Ser Ser Leu Cys Trp
            1405                1410                1415

TAT GAC TAT ATT GAA GTA AGA GAC GGG TAC TGG AGA AAA TCA CCT CTC       1904
Tyr Asp Tyr Ile Glu Val Arg Asp Gly Tyr Trp Arg Lys Ser Pro Leu
            1420                1425                1430

CTT GGT AGA TTC TGT GGG GAC AAA TTG CCT GAA GTT CTT ACT TCT ACA       1952
Leu Gly Arg Phe Cys Gly Asp Lys Leu Pro Glu Val Leu Thr Ser Thr
            1435                1440                1445

GAC AGC AGA ATG TGG ATT GAG TTT CGT AGC AGC AGT AAT TGG GTA GGA       2000
Asp Ser Arg Met Trp Ile Glu Phe Arg Ser Ser Ser Asn Trp Val Gly
1450            1455                1460                1465

AAA GGC TTT GCA GCT GTC TAT GAA GCG ATC TGT GGA GGT GAG ATA CGT       2048
Lys Gly Phe Ala Ala Val Tyr Glu Ala Ile Cys Gly Gly Glu Ile Arg
            1470                1475                1480

AAA AAT GAA GGA CAG ATT CAG TCT CCC AAT TAT CCT GAT GAC TAT CGC       2096
Lys Asn Glu Gly Gln Ile Gln Ser Pro Asn Tyr Pro Asp Asp Tyr Arg
            1485                1490                1495

CCG ATG AAA GAA TGT GTG TGG AAA ATA ACA GTG TCT GAG AGC TAC CAC       2144
Pro Met Lys Glu Cys Val Trp Lys Ile Thr Val Ser Glu Ser Tyr His
            1500                1505                1510

GTC GGG CTG ACC TTT CAG TCC TTT GAG ATT GAA AGA CAT GAC AAT TGT       2192
Val Gly Leu Thr Phe Gln Ser Phe Glu Ile Glu Arg His Asp Asn Cys
            1515                1520                1525

GCT TAT GAC TAC CTG GAA GTT AGA GAT GGA ACC AGT GAA AAT AGC CCT       2240
Ala Tyr Asp Tyr Leu Glu Val Arg Asp Gly Thr Ser Glu Asn Ser Pro
1530            1535                1540                1545

TTG ATA GGG CGT TTC TGT GGT TAT GAC AAA CCT GAA GAC ATA AGA TCT       2288
```

```
                                                -continued

Leu Ile Gly Arg Phe Cys Gly Tyr Asp Lys Pro Glu Asp Ile Arg Ser
             1550                1555               1560

ACC TCC AAT ACT TTG TGG ATG AAG TTT GTT TCT GAC GGA ACT GTG AAC       2336
Thr Ser Asn Thr Leu Trp Met Lys Phe Val Ser Asp Gly Thr Val Asn
             1565                1570               1575

AAA GCA GGG TTT GCT GCT AAC TTT TTT AAA GAG GAA GAT GAG TGT GCC       2384
Lys Ala Gly Phe Ala Ala Asn Phe Phe Lys Glu Glu Asp Glu Cys Ala
             1580                1585               1590

AAA CCT GAC CGT GGA GGC TGT GAG CAG CGA TGT CTG AAC ACT CTG GGC       2432
Lys Pro Asp Arg Gly Gly Cys Glu Gln Arg Cys Leu Asn Thr Leu Gly
             1595                1600               1605

AGT TAC CAG TGT GCC TGT GAG CCT GGC TAT GAG CTG GGC CCA GAC AGA       2480
Ser Tyr Gln Cys Ala Cys Glu Pro Gly Tyr Glu Leu Gly Pro Asp Arg
1610                1615                1620                1625

AGG AGC TGT GAA GCT GCT TGT GGT GGA CTT CTT ACC AAA CTT AAC GGC       2528
Arg Ser Cys Glu Ala Ala Cys Gly Gly Leu Leu Thr Lys Leu Asn Gly
             1630                1635               1640

ACC ATA ACC ACC CCT GGC TGG CCC AAG GAG TAC CCT CCT AAT AAG AAC       2576
Thr Ile Thr Thr Pro Gly Trp Pro Lys Glu Tyr Pro Pro Asn Lys Asn
             1645                1650               1655

TGT GTG TGG CAA GTG GTT GCA CCA ACC CAG TAC AGA ATT TCT GTG AAG       2624
Cys Val Trp Gln Val Val Ala Pro Thr Gln Tyr Arg Ile Ser Val Lys
             1660                1665               1670

TTT GAG TTT TTT GAA TTG GAA GGC AAT GAA GTT TGC AAA TAT GAT TAT       2672
Phe Glu Phe Phe Glu Leu Glu Gly Asn Glu Val Cys Lys Tyr Asp Tyr
             1675                1680               1685

GTG GAG ATC TGG AGT GGT CTT TCC TCT GAG TCT AAA CTG CAT GGC AAA       2720
Val Glu Ile Trp Ser Gly Leu Ser Ser Glu Ser Lys Leu His Gly Lys
1690                1695                1700                1705

TTC TGT GGC GCT GAA GTG CCT GAA GTG ATC ACA TCC CAG TTC AAC AAT       2768
Phe Cys Gly Ala Glu Val Pro Glu Val Ile Thr Ser Gln Phe Asn Asn
             1710                1715               1720

ATG AGA ATT GAA TTC AAA TCT GAC AAT ACT GTA TCC AAG AAG GGC TTC       2816
Met Arg Ile Glu Phe Lys Ser Asp Asn Thr Val Ser Lys Lys Gly Phe
             1725                1730               1735

AAA GCA CAT TTT TTC TCA GAC AAA GAT GAA TGC TCT AAG GAT AAT GGT       2864
Lys Ala His Phe Phe Ser Asp Lys Asp Glu Cys Ser Lys Asp Asn Gly
             1740                1745               1750

GGA TGT CAG CAC GAA TGT GTC AAC ACG ATG GGG AGC TAC ATG TGT CAA       2912
Gly Cys Gln His Glu Cys Val Asn Thr Met Gly Ser Tyr Met Cys Gln
             1755                1760               1765

TGC CGT AAT GGA TTT GTG CTA CAT GAC AAT AAA CAT GAT TGC AAG GAA       2960
Cys Arg Asn Gly Phe Val Leu His Asp Asn Lys His Asp Cys Lys Glu
1770                1775                1780                1785

GCT GAG TGT GAA CAG AAG ATC CAC AGT CCA AGT GGC CTC ATC ACC AGT       3008
Ala Glu Cys Glu Gln Lys Ile His Ser Pro Ser Gly Leu Ile Thr Ser
             1790                1795               1800

CCC AAC TGG CCA GAC AAG TAC CCA AGC AGG AAA GAA TGC ACT TGG GAA       3056
Pro Asn Trp Pro Asp Lys Tyr Pro Ser Arg Lys Glu Cys Thr Trp Glu
             1805                1810               1815

ATC AGC GCC ACT CCC GGC CAC CGA ATC AAA TTA GCC TTT AGT GAA TTT       3104
Ile Ser Ala Thr Pro Gly His Arg Ile Lys Leu Ala Phe Ser Glu Phe
             1820                1825               1830

GAG ATT GAG CAG CAT CAA GAA TGT GCT TAT GAC CAC TTA GAA GTA TTT       3152
Glu Ile Glu Gln His Gln Glu Cys Ala Tyr Asp His Leu Glu Val Phe
             1835                1840               1845

GAT GGA GAA ACA GAA AAG TCA CCG ATT CTT GGA CGA CTA TGT GGC AAC       3200
Asp Gly Glu Thr Glu Lys Ser Pro Ile Leu Gly Arg Leu Cys Gly Asn
1850                1855                1860                1865

AAG ATA CCA GAT CCC CTT GTG GCT ACT GGA AAT AAA ATG TTT GTT CGG       3248
```

-continued

| | | | | | | | | | | | | | |
|---|---|---|---|---|---|---|---|---|---|---|---|---|---|
| Lys | Ile | Pro | Asp | Pro | Leu | Val | Ala | Thr | Gly | Asn | Lys | Met | Phe | Val | Arg |
| | | | 1870 | | | | 1875 | | | | 1880 | | |

```
TTT GTT TCT GAT GCA TCT GTT CAA AGA AAA GGC TTT CAA GCC ACA CAT   3296
Phe Val Ser Asp Ala Ser Val Gln Arg Lys Gly Phe Gln Ala Thr His
            1885                1890                1895

TCT ACA GAG TGT GGC GGA CGA TTG AAA GCA GAA TCA AAA CCA AGA GAT   3344
Ser Thr Glu Cys Gly Gly Arg Leu Lys Ala Glu Ser Lys Pro Arg Asp
        1900                1905                1910

CTG TAC TCA CAT GCT CAG TTT GGT GAT AAC AAC TAC CCA GGA CAG GTT   3392
Leu Tyr Ser His Ala Gln Phe Gly Asp Asn Asn Tyr Pro Gly Gln Val
        1915                1920                1925

GAC TGT GAA TGG CTA TTA GTA TCA GAA CGG GGC TCT CGA CTT GAA TTA   3440
Asp Cys Glu Trp Leu Leu Val Ser Glu Arg Gly Ser Arg Leu Glu Leu
1930            1935                1940                1945

TCC TTC CAG ACA TTT GAA GTG GAG GAA GAA GCA GAC TGT GGC TAT GAC   3488
Ser Phe Gln Thr Phe Glu Val Glu Glu Glu Ala Asp Cys Gly Tyr Asp
            1950                1955                1960

TAT GTG GAG CTC TTT GAT GGT CTT GAT TCA ACA GCT GTG GGG CTT GGT   3536
Tyr Val Glu Leu Phe Asp Gly Leu Asp Ser Thr Ala Val Gly Leu Gly
        1965                1970                1975

CGA TTC TGT GGA TCC GGG CCA CCA GAA GAG ATT TAT TCA ATT GGA GAT   3584
Arg Phe Cys Gly Ser Gly Pro Pro Glu Glu Ile Tyr Ser Ile Gly Asp
        1980                1985                1990

TCA GTT TTA ATT CAT TTC CAC ACT GAT GAC ACA ATC AAC AAG AAG GGA   3632
Ser Val Leu Ile His Phe His Thr Asp Asp Thr Ile Asn Lys Lys Gly
        1995                2000                2005

TTT CAT ATA AGA TAC AAA AGC ATA AGA TAT CCA GAT ACC ACA CAT ACC   3680
Phe His Ile Arg Tyr Lys Ser Ile Arg Tyr Pro Asp Thr Thr His Thr
2010            2015                2020                2025

AAA AAA TAA CACCAAAACC TCTGTCAGAA CACAAAGGAA TGTGCATAAT           3729
Lys Lys *
GGAGAGAAGA CATATTTTTT TTAAAACTGA AGATATTGGC ACAAATGTTT TATACAAAGA 3789

GTTTGAACAA AAAATCCCTG TAAGACCAGA ATTATCTTTG TACTAAAAGA GAAGTTTCCA 3849

GCAAAACCCT CATCAGCATT ACAAGGATAT TTGAACTCCA TGCTTGATGG TATTAATAAA 3909

GCTGGTGAAA                                                        3919
```

(2) INFORMATION FOR SEQ ID NO:5:

(i) SEQUENCE CHARACTERISTICS:
        (A) LENGTH: 1013 amino acids
        (B) TYPE: amino acid
        (D) TOPOLOGY: linear (ii) MOLECULE TYPE: protein (xi) SEQUENCE DESCRIPTION: SEQ ID NO:5:

```
Met Gly Leu Gly Thr Leu Ser Pro Arg Met Leu Val Trp Leu Val Ala
1               5                   10                  15

Ser Gly Ile Val Phe Tyr Gly Glu Leu Trp Val Cys Ala Gly Leu Asp
            20                  25                  30

Tyr Asp Tyr Thr Phe Asp Gly Asn Glu Glu Asp Lys Thr Glu Thr Ile
        35                  40                  45

Asp Tyr Lys Asp Pro Cys Lys Ala Ala Val Phe Trp Gly Asp Ile Ala
    50                  55                  60

Leu Asp Asp Glu Asp Leu Asn Ile Phe Gln Ile Asp Arg Thr Ile Asp
65                  70                  75                  80

Leu Thr Gln Asn Pro Phe Gly Asn Leu Gly His Thr Thr Gly Gly Leu
            85                  90                  95

Gly Asp His Ala Met Ser Lys Lys Arg Gly Ala Leu Tyr Gln Leu Ile
```

```
                    100                 105                 110
Asp Arg Ile Arg Arg Ile Gly Phe Gly Leu Glu Gln Asn Asn Thr Val
            115                 120                 125
Lys Gly Lys Val Pro Leu Gln Phe Ser Gly Gln Asn Glu Lys Asn Arg
        130                 135                 140
Val Pro Arg Ala Ala Thr Ser Arg Thr Glu Arg Ile Trp Pro Gly Gly
145                 150                 155                 160
Val Ile Pro Tyr Val Ile Gly Gly Asn Phe Thr Gly Ser Gln Arg Ala
                165                 170                 175
Met Phe Lys Gln Ala Met Arg His Trp Glu Lys His Thr Cys Val Thr
            180                 185                 190
Phe Ile Glu Arg Ser Asp Glu Glu Ser Tyr Ile Val Phe Thr Tyr Arg
        195                 200                 205
Pro Cys Gly Cys Cys Ser Tyr Val Gly Arg Arg Gly Asn Gly Pro Gln
210                 215                 220
Ala Ile Ser Ile Gly Lys Asn Cys Asp Lys Phe Gly Ile Val Val His
225                 230                 235                 240
Glu Leu Gly His Val Ile Gly Phe Trp His Glu His Thr Arg Pro Asp
                245                 250                 255
Arg Asp Asn His Val Thr Ile Ile Arg Glu Asn Ile Gln Pro Gly Gln
            260                 265                 270
Glu Tyr Asn Phe Leu Lys Met Glu Pro Gly Glu Val Asn Ser Leu Gly
        275                 280                 285
Glu Arg Tyr Asp Phe Asp Ser Ile Met His Tyr Ala Arg Asn Thr Phe
290                 295                 300
Ser Arg Gly Met Phe Leu Asp Thr Ile Leu Pro Ser Arg Asp Asp Asn
305                 310                 315                 320
Gly Ile Arg Pro Ala Ile Gly Gln Arg Thr Arg Leu Ser Lys Gly Asp
                325                 330                 335
Ile Ala Gln Ala Arg Lys Leu Tyr Arg Cys Pro Ala Cys Gly Glu Thr
            340                 345                 350
Leu Gln Glu Ser Asn Gly Asn Leu Ser Ser Pro Gly Phe Pro Asn Gly
        355                 360                 365
Tyr Pro Ser Tyr Thr His Cys Ile Trp Arg Val Ser Val Thr Pro Gly
370                 375                 380
Glu Lys Ile Val Leu Asn Phe Thr Thr Met Asp Leu Tyr Lys Ser Ser
385                 390                 395                 400
Leu Cys Trp Tyr Asp Tyr Ile Glu Val Arg Asp Gly Tyr Trp Arg Lys
                405                 410                 415
Ser Pro Leu Leu Gly Arg Phe Cys Gly Asp Lys Leu Pro Glu Val Leu
            420                 425                 430
Thr Ser Thr Asp Ser Arg Met Trp Ile Glu Phe Arg Ser Ser Ser Asn
        435                 440                 445
Trp Val Gly Lys Gly Phe Ala Ala Val Tyr Glu Ala Ile Cys Gly Gly
450                 455                 460
Glu Ile Arg Lys Asn Glu Gly Gln Ile Gln Ser Pro Asn Tyr Pro Asp
465                 470                 475                 480
Asp Tyr Arg Pro Met Lys Glu Cys Val Trp Lys Ile Thr Val Ser Glu
                485                 490                 495
Ser Tyr His Val Gly Leu Thr Phe Gln Ser Phe Glu Ile Glu Arg His
            500                 505                 510
Asp Asn Cys Ala Tyr Asp Tyr Leu Glu Val Arg Asp Gly Thr Ser Glu
        515                 520                 525
```

-continued

```
Asn Ser Pro Leu Ile Gly Arg Phe Cys Gly Tyr Asp Lys Pro Glu Asp
    530                 535                 540

Ile Arg Ser Thr Ser Asn Thr Leu Trp Met Lys Phe Val Ser Asp Gly
545                 550                 555                 560

Thr Val Asn Lys Ala Gly Phe Ala Ala Asn Phe Phe Lys Glu Glu Asp
                565                 570                 575

Glu Cys Ala Lys Pro Asp Arg Gly Gly Cys Glu Gln Arg Cys Leu Asn
            580                 585                 590

Thr Leu Gly Ser Tyr Gln Cys Ala Cys Glu Pro Gly Tyr Glu Leu Gly
        595                 600                 605

Pro Asp Arg Arg Ser Cys Glu Ala Ala Cys Gly Gly Leu Leu Thr Lys
    610                 615                 620

Leu Asn Gly Thr Ile Thr Thr Pro Gly Trp Pro Lys Glu Tyr Pro Pro
625                 630                 635                 640

Asn Lys Asn Cys Val Trp Gln Val Val Ala Pro Thr Gln Tyr Arg Ile
                645                 650                 655

Ser Val Lys Phe Glu Phe Phe Glu Leu Glu Gly Asn Glu Val Cys Lys
            660                 665                 670

Tyr Asp Tyr Val Glu Ile Trp Ser Gly Leu Ser Ser Glu Ser Lys Leu
        675                 680                 685

His Gly Lys Phe Cys Gly Ala Glu Val Pro Glu Val Ile Thr Ser Gln
    690                 695                 700

Phe Asn Asn Met Arg Ile Glu Phe Lys Ser Asp Asn Thr Val Ser Lys
705                 710                 715                 720

Lys Gly Phe Lys Ala His Phe Phe Ser Asp Lys Asp Glu Cys Ser Lys
                725                 730                 735

Asp Asn Gly Gly Cys Gln His Glu Cys Val Asn Thr Met Gly Ser Tyr
            740                 745                 750

Met Cys Gln Cys Arg Asn Gly Phe Val Leu His Asp Asn Lys His Asp
        755                 760                 765

Cys Lys Glu Ala Glu Cys Glu Gln Lys Ile His Ser Pro Ser Gly Leu
    770                 775                 780

Ile Thr Ser Pro Asn Trp Pro Asp Lys Tyr Pro Ser Arg Lys Glu Cys
785                 790                 795                 800

Thr Trp Glu Ile Ser Ala Thr Pro Gly His Arg Ile Lys Leu Ala Phe
                805                 810                 815

Ser Glu Phe Glu Ile Glu Gln His Gln Glu Cys Ala Tyr Asp His Leu
            820                 825                 830

Glu Val Phe Asp Gly Glu Thr Glu Lys Ser Pro Ile Leu Gly Arg Leu
        835                 840                 845

Cys Gly Asn Lys Ile Pro Asp Pro Leu Val Ala Thr Gly Asn Lys Met
    850                 855                 860

Phe Val Arg Phe Val Ser Asp Ala Ser Val Gln Arg Lys Gly Phe Gln
865                 870                 875                 880

Ala Thr His Ser Thr Glu Cys Gly Gly Arg Leu Lys Ala Glu Ser Lys
                885                 890                 895

Pro Arg Asp Leu Tyr Ser His Ala Gln Phe Gly Asp Asn Asn Tyr Pro
            900                 905                 910

Gly Gln Val Asp Cys Glu Trp Leu Leu Val Ser Glu Arg Gly Ser Arg
        915                 920                 925

Leu Glu Leu Ser Phe Gln Thr Phe Glu Val Glu Glu Ala Asp Cys
    930                 935                 940

Gly Tyr Asp Tyr Val Glu Leu Phe Asp Gly Leu Asp Ser Thr Ala Val
945                 950                 955                 960
```

```
Gly Leu Gly Arg Phe Cys Gly Ser Gly Pro Pro Glu Glu Ile Tyr Ser
            965                 970                 975

Ile Gly Asp Ser Val Leu Ile His Phe His Thr Asp Asp Thr Ile Asn
        980                 985                 990

Lys Lys Gly Phe His Ile Arg Tyr Lys Ser Ile Arg Tyr Pro Asp Thr
        995                 1000                1005

Thr His Thr Lys Lys
    1010
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:6:

CCAGCTTAAC CTGTTCACAC                                      20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:7:

AACTCTACTT CCACTTCATC                                      20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:8:

TCAGAACAGA AAGGAATGTG                                      20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:9:

GACCACTATT CCACATCACC                                      20

(2) INFORMATION FOR SEQ ID NO:10:

-continued

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:10:

TCTTGCAGTC AGTTGCTTTG CTGG                                       24

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:11:

TAGTGCGGCC GCACATTCCT TTGTGTTC                                   28

(2) INFORMATION FOR SEQ ID NO:12:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Cys Tyr Ile Arg Tyr Lys Ser Ile Arg Tyr Pro Glu Thr Met His Ala
1               5                   10                  15

Lys Asn (2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Cys His Ile Arg Tyr Lys Ser Ile Arg Tyr Pro Asp Thr Thr His Thr
1               5                   10                  15

Lys Lys
```

MAMMALIAN TOLLOID-LIKE GENE AND PROTEIN

CROSS-REFERENCE TO RELATED APPLICATIONS

This application claims the benefit of Provisional Patent Application Number 60/018,684 filed May 30, 1996.

STATEMENT REGARDING FEDERALLY SPONSORED RESEARCH OR DEVELOPMENT

Not applicable.

BACKGROUND OF THE INVENTION

The present invention relates to the field of bone morphogenetic proteins and more particularly to a gene in the BMP-1/Tld family of genes.

Bone formation in mammals such as mice and humans is governed by a set of bone morphogenetic proteins (BMP). Of the seven BMPs known to participate in osteogenesis, six (designated BMP-2 through BMP-7) belong to the TGF-β super family. The seventh BMP (designated BMP-1) is not TGF-β-like, but instead appears to derive from a different gene family. The BMP-1 gene family members typically contain the following domains: an astacin-like metalloprotease domain, one or more EGF-like motifs which in other proteins are thought to bind $Ca^{++}$, and a number of CUB domains. A CUB domain is a motif that mediates protein-protein interactions in complement components C1r/C1s which has also been identified in various proteins involved in developmental processes. BMP-1 was described, at the nucleotide sequence level, by Wozney, J. M., et al., *Science* 242:1528–1534 (1988).

The mammalian BMP-1 domain structure is shared by proteins found in other non-mammalian species. These proteins include Drosophila tolloid (Tld) (Shimell, M. J., *Cell* 67:469–481 (1991)), a tolloid-like Drosophila gene product (Tlr-1 or tolkin) (Nguyen, T., *Dev. Biol.* 166:569–586 (1994) and Finelli, A. L., et al., *Genetics* 141:271–281 (1995)), a sea urchin BMP-1 homolog (suBMP-1) (Hwang, S.-P., et al., *Development* 120:559–568 (1994)), two related sea urchin developmental gene products, SpAN and BP10 (Reynolds, S. D., et al., *Development* 114:769–786 (1992) and Lepage, T., et al., *Development* 114:147–164 (1992)), a Xenopus BMP-1 (xBMP-1) (Maeno, M. et al., *Gene* 134:257–261 (1993) and a mammalian tolloid (mTld) (Takahara, K. et al., *J. Biol. Chem.* 269:32572–32578 (1994)). A tolloid-like gene (xolloid) obtained from Xenopus has been briefly mentioned in passing in a article reviewing the astacin family of metalloproteases. Bond, J. S. and R. J. Benynon, *Protein Science* 4:1247–1261 at 1249 (1995), but data relating to the gene itself has not been published. Some of the nucleic acid sequences of the genes that encode these proteins are known. The mammalian BMP1 gene encodes both the BMP-1 protein and the mTld protein, albeit on two distinct, alternately spliced mRNA molecules. The papers mentioned in this paragraph are incorporated herein by reference.

BRIEF SUMMARY OF THE INVENTION

The present invention is summarized in that a novel mammalian tolloid-like gene product (mTll) and its cognate gene, which is distinct from mTld and from all other known BMP-1-related proteins and genes, are described. The murine and human versions of the gene are reported.

It is an object of the present invention to provide a gene and gene product involved in the deposition of extracellular matrix in vertebrates (e.g., in osteogenesis).

It is another object of the present invention to provide a target molecule for rational development of a drug for inhibiting activity of the tolloid-like genes to treat fibrosis, scarring, keloids, surgical adhesions, and the like.

It is yet another object of the present invention to provide a recombinant DNA construct, and a protein encoded by the construct, for use in accelerated wound and fracture healing.

It is still another object of the present invention to provide a marker gene that maps to the central portion of mouse chromosome 8.

It is yet another object of the present invention to provide a marker gene that maps to the 4q32-4q33 region of human chromosome 4.

It is still another object of the present invention to provide a nucleotide sequence that functions as a probe for a non-BMP-1 bone morphogenetic protein gene in mammalian cells.

It is a feature of the present invention that the murine gene described contains a novel simple sequence repeat in the 3'-untranslated region of the gene.

Other objects, features, and advantages of the present invention will become apparent upon consideration of the following detailed description considered in conjunction with the accompanying drawings.

BRIEF DESCRIPTION OF THE SEVERAL VIEWS OF THE DRAWINGS

FIG. 2 aligns the amino acid sequence of the disclosed mTll gene to that of the mTld gene. The domain structure common to both proteins is shown schematically. Domains are represented as in FIG. 1. Alignment was performed using the GAP program (Genetics Computer Group, Madison, Wis.), with a GAP weight of 3.0 and GAP length weight of 0.1, with some additional manual alignment of putative signal peptide sequences. Cysteines are boxed, potential Asn-linked glycosylation sites are underlined and the metalloendopeptidase active site motif HEXXH is enclosed by a dashed box.

DETAILED DESCRIPTION OF THE INVENTION

A substantially pure preparation of the mammalian tolloid-like (mTll) cDNA was isolated from mice by probing a cDNA library prepared from embryo fibroblasts of mouse strain BMP-1$^{tm1blh}$ with an approximately 330 base-pair AatII-DrdI restriction fragment of the mouse BMP-1 gene and screening at low stringency, as is described in more detail in the examples below. BMP-1$^{tm1blh}$ is a BMP-1 knockout (KO) mouse that is homozygous for a null allele of the BMP-1 gene. The probe, shown in SEQ ID NO:1, corresponds to a segment of the 360 base pair portion of the BMP-1 gene that is absent from the BMP-1$^{tm1blh}$ knockout strain. Since BMP-1 is absent from the cDNA library, the screen uncovered only sequences related to, but distinct from, BMP-1 at the DNA sequence level.

Figure 1:
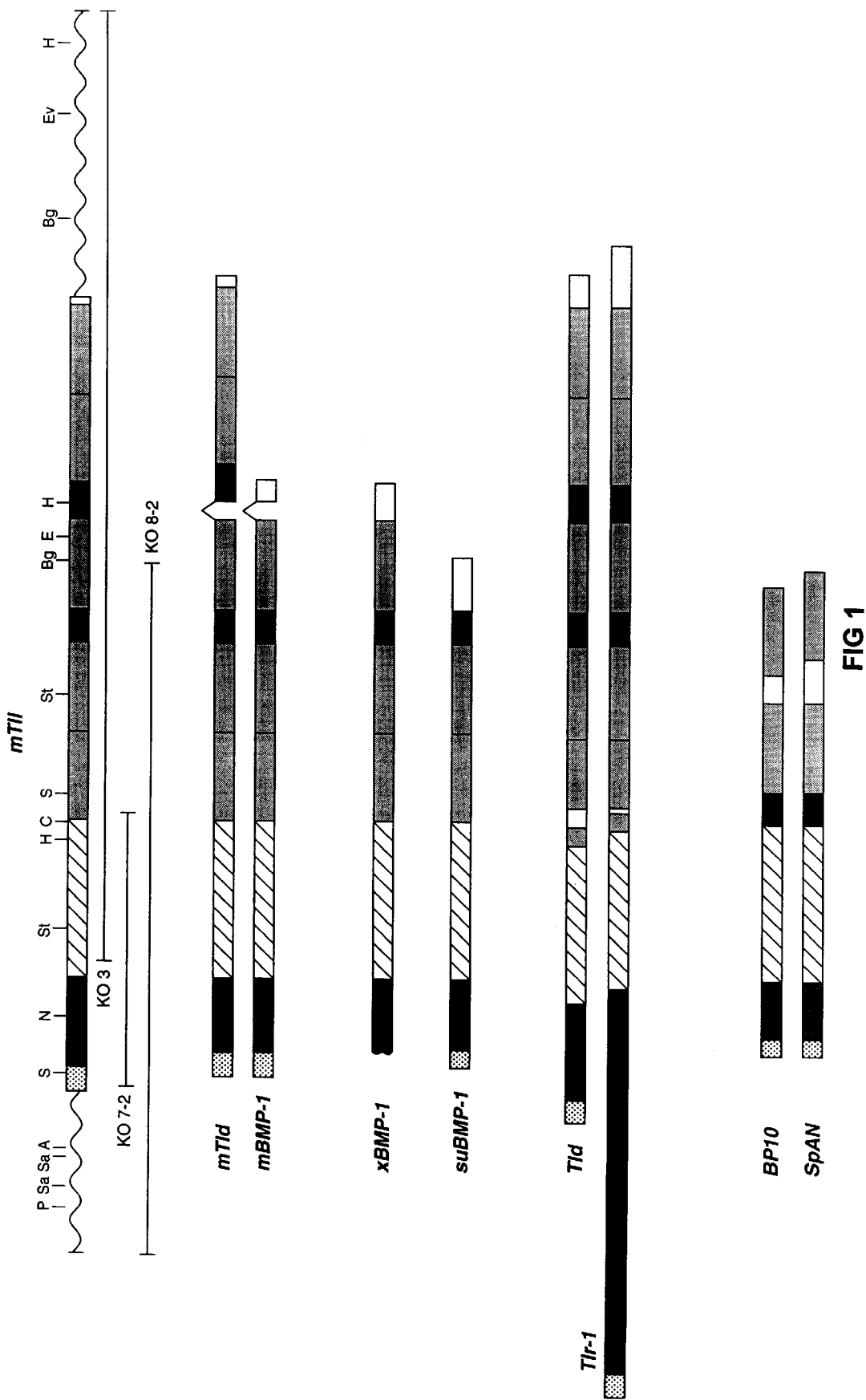
FIG. 1 presents a map of the murine mTll cDNA including 5'- and 3'-untranslated portions thereof. Also aligned beneath the mTll cDNA for comparison are schematic representations of cDNA clones of related genes, drawn to the same scale as mTll. Portions of the cDNA corresponding to domains of the gene product are highlighted. Stippled, darkly shaded, striped, lightly shaded, and black boxes represent signal peptide, proregion, metalloprotease, CUB, and EGF domains, respectively. White boxes represent domains unique to the various proteins. Wavy lines represent 5'- and 3'-untranslated regions. Abbreviations: mTld, mammalian tolloid; mBMP-1, mammalian BMP-1; xBMP-1, xenopus BMP-1; suBMP-1, sea urchin BMP-1; Tld, Drosophila tolloid; Tlr-1, Drosophila tolloid-related gene; SpAN and BP10, related sea urchin developmental genes. Restriction enzymes include: Bg, BglII; C, ClaI; E, EcoRI; H, HincII; N, NcoI; S, SmaI; St, StuI.
Figure 3:
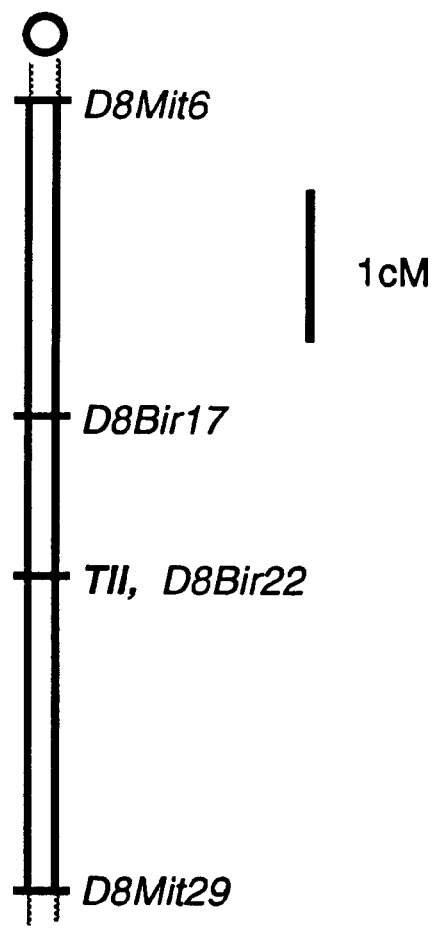
FIG. 3 shows a schematic map of the central portion of mouse chromosome 8. The Map Manager program (Manly K., "A Macintosh Program for Storage and Analysis of Experimental Genetic Mapping Data," *Mammalian Genome* 4:301–313 (1993) compared segregation data for Tll and for other loci from the TJL BSS backcross panel, performed the linkage analysis and generated the map. The TJL BSS backcross panel data are available on the Jackson Laboratories Public Data Base (http://www.jax.org/Resources/documents/cmdata).

A single region of the genome was uncovered in the screening (see FIG. 1). Overlapping cDNA clones KO 3 and KO 7-2, obtained in the initial screen as substantially pure preparations covered much, but not all, of the coding sequence. Screening was performed under low stringency using standard protocols (Ausubel, F. M., et al., *Current Protocols in Molecular Biology*, Wiley, New York (1987) CA). The remainder of the coding sequence was obtained by re-screening the embryo fibroblast cDNA library at high stringency to reveal an additional clone (KO 8-2) that extended into the 5'-untranslated portion of the gene. Clone KO 8-2 was also obtained as a substantially pure preparation.

One of ordinary skill in the art can join the separate cloned sequences together, as the inventors have done, to produce the complete full-length cDNA shown in SEQ ID NO:2. Presented herein as SEQ ID NO:2 is an open reading frame of 3039 base pairs flanked by 5'- and 3'-untranslated sequences. The open reading frame encodes a mammalian tolloid-like protein termed mTll. The sequence presented herein represents the combined nucleic acid sequences of three cDNA clones (KO 3, KO 7-2 and KO 8-2). In the 3' untranslated region of the mTll gene is a previously unreported simple sequence repeat (SSR). The SSR has the following sequence: $(GT)_{20}GC(GT)_7 GC(GT)_7GCAT(GT)_3GCAT(GT)_3$ (shown at nucleotides 4148 to 4239 in SEQ ID NO:2). The sequence data presented in SEQ ID NO:2 will be available at Genbank Accession Number U34042.

A preparation of DNA molecules containing an mTll gene sequence from any source is considered substantially pure if more than 90% of any cellular material of any host cell in which the DNA has resided has been removed from the DNA preparation. Cellular material can be removed from a nucleic acid preparation, for example, by using a commercial purification kit such as is available from Qiagen (Chatsworth, Calif.). It is preferred that greater than 10% of the nucleic acid molecules in a nucleic acid preparation comprise the complete or partial mTll gene or a portion thereof. More preferably, greater than 50%, and yet more preferably, greater than 90%, of the nucleic acid molecules comprise the complete or partial sequence.

It is noted that additional genes having some relation to mTll and other members of the BMP-1 family might be isolated from double null embryo cDNA libraries lacking both BMP-1/mTld and mTll using a comparable screening strategy. Such double null mutant animals could be produced by mating animals heterozygous at each of the two loci.

The murine mTll gene maps to central chromosome 8 close to D8Bir22, which was placed at position 31 in the 1994 chromosome 8 committee report (Ceci, J. D., "Mouse Chromosome 8," *Mammalian Genome* 5:S124–138 (1994)). This same general chromosomal region is the map site of four genetic defects that lead to apparent developmental abnormalities: Hook (Hk), Adrenocortical dysplasia (Acd), Quinky (Q), and Proportional dwarf (pdw). BMP-1, in contrast, maps to mouse chromosome 14 (Ceci, J. D., et al., "An interspecific backcross linkage map of the proximal half of mouse chromosome 14," *Genomics* 6:673–678 (1990)).

A proposed murine mTll protein domain structure, predicted from sequence similarities to the m-tolloid protein product, is shown in FIG. 2. In view of the similarity to other tolloid-like proteins, it is expected that the product encoded by the disclosed mTll gene will be a protease having a key role in development and in homeostatic processes such as wound healing. It is likely that the protein is involved in maturation of extracellular matrix precursors into macromolecular structures. The protein may also have a role in activation of growth factors in vivo and in vitro, and may accelerate developmental and homeostatic processes when an effective amount of the protein is administered to a tissue. On the other hand, if the mTll protein function is inhibited, such processes may themselves be inhibited, which property can be exploited advantageously upon delivery of an effective amount of an inhibitor to prevent fibrosis and excess scarring or other abnormalities of wound healing. An effective amount of the protein to be delivered to a target site for activating developmental and homeostatic properties can readily be determined by testing a range of amounts of the protein on a selected veterinary species or on a model species having acknowledged biochemical or physiological similarity to humans. In the case of skin wound healing, for example, porcine skin is a suitable model for human skin. Likewise, an effective amount of an inhibitor of the Tll protein can also be determined. An effective amount is an amount effective upon administration to a wound that reduces the occurrence of fibrosis, scarring or keloids compared to an untreated wound, where the assessment of fibrosis, scarring or keloids is made according to accepted clinical or veterinary standards. Such a test is preferably performed in a model system generally accepted as having relevance to human skin.

The ability to work with proteins of the BMP system has been hampered by the fact that the proteins are typically present in very small amounts in animal tissues. It is herein demonstrated (see, infra) that mTll, a previously unknown gene, can be cloned into a suitable expression vector containing a transcriptional promoter effective in a suitable host cell, introduced into and expressed in the suitable host cells, and purified in a native configuration, all using conventional methods. The protein thus expressed can remain inside the host cell or can be secreted to the extracellular growth medium, if a suitable signal sequence is provided on the construct. The protein can be purified from the cell or from the growth medium by conventional methods.

A suitable promoter of transcription is the baculovirus very late promoter found on vector pFASTBac1, which vector is commercially available from Gibco-BRL. Another suitable promoter is baculovirus immediate early promoter such as is found on the pAcPIE1 vector (Novagen, Madison, Wis.). Any other advantageous expression elements such as enhancers, terminators, and the like, as are known to the art, can be included on the suitable expression vector. A suitable host would be insect tissue culture cells, such as cell line Sf21, Sf9, or High Five (Invitrogen, San Diego, Calif.).

Suitable portions of the gene comprising less than the full coding sequence can also be advantageously cloned into the suitable expression vector to form a recombinant genetic construct. It is understood that a construct prepared in accordance with the invention, need not necessarily contain the entire mTll locus or coding region, but could contain one or more portions thereof encoding a desired function, or containing a portion of the gene having other useful properties, for example, complementarity to a desired genomic sequence. It is understood by those of ordinary skill that certain variation in the size or sequence of the mTll protein (and in the corresponding genetic material encoding the mTll protein) will not interfere with the functions thereof. Such modified forms can be engineered using known methods that may be advantageously employed when constructing genetic constructs containing the complete or partial mTll gene, and in proteins encoded thereby.

Such changes, modifications, additions and deletions are contemplated to fall within the scope of the present invention, as long as the protein retains a desired function known to be associated with other members of this protein family. The protein is competent if it retains an ability to cleave laminin-5 in a standard assay for such cleavage. It is also desired that the protein retain a C-proteinase activity against procollagen as was described for BMP-1 by Kessler, E., et al., Science 271:360–362 (1996), incorporated herein by reference. One of ordinary skill is familiar with the necessary controls that should accompany any such assay. It may, alternatively, be desired that the protein lose a certain function as a result of such a change, and such a situation is also envisioned to be within the scope of the present invention.

A substantially pure preparation of the protein thus produced is defined as a preparation wherein the laminin-5-cleaving activity of the mTll protein is not affected by the presence of other proteins or molecules in the preparation. Depending upon the use to which the protein will be put, it may be that the mTll protein accounts for at least 10%, preferably at least 50%, more preferably at least 75%, and most preferably at least 95% of the protein in the substantially pure protein preparation. The protein preparation can be enhanced for the protein of interest by labeling the protein with an affinity tag and passing the preparation over a column having an affinity for the tag. It is also possible to employ a processing tag such that a properly processed form of the protein (lacking the cleaved proregion) can be eluted from a column loaded with a crude preparation.

The mTll translation product (SEQ ID NO:3) predicted from the DNA sequence has a predicted molecular weight of 114,532 (pI 6.15). If the translation product is cleaved between the proregion and the protease domain at the boundary shown in FIG. 2, the predicted molecular weight for the mature protease would be 98,007 (pI 6.18).

When the murine mTll protein sequence is compared to other tolloid-like genes, no obvious homology exists between the proregion of either of the two mammalian proteins (mTld and mTll) and the proregion of either of the two Drosophila proteins (Tld or Tlr-1). The protease domain of mTll was 66% similar (47% identical) to Tld and was 69% similar (52% identical) to Tlr-1. mTll is slightly more similar in sequence to both Drosophila proteins than is mTld, and there is no obvious correlation between a particular member of the mammalian protein pair and a particular member of the Drosophila protein pair. An aligned pair of amino acids are "similar" if they have a threshold of similarity above 0.5 by the scoring system of Schwartz and Dayhoff, Atlas of Protein Sequence and Structure, Dayhoff, M. O., ed., National Biomedical Research Foundation, Washington, D.C., p. 353–358 (1979).

The mTll mRNA transcript appears not to be alternatively spliced since only a single transcript was detected using a fragment of clone KO 3 internal to the coding region as a probe (SEQ ID NO:2, nucleotides 1113 to 2745) and because only a single mTll cDNA was isolated during the cDNA library screenings.

Relatively strong mTll mRNA expression was observed in adult brain and kidney, with somewhat lower expression in RNA from lung and skeletal muscle, and very low expression in RNA from heart and testes. No signal was apparent for spleen or liver. After the Northern Blot was exposed for 60 hours, a very faint signal could be detected for liver, although no signal from spleen was detected.

The mRNA expression pattern of mTll differs from that previously reported for BMP-1 transcripts and mTld transcripts. Low expression levels are seen even in seven day post-coitum total embryo RNA. The mRNA level increases slightly at eleven days of development, peaks at relatively high levels at fifteen days, and then decreases in seventeen day embryos. In contrast, BMP-1 and mTld transcripts were observed at higher levels in seven day embryos than in eleven day embryos. The same blot was used to monitor the mTll, BMP-1, and mTld transcript levels.

The mTll mRNA transcripts were detected throughout embryonic development in the period of 9.5 to 15.5 days post-coitum. As was previously observed with mTld RNA, mTll signals were observed throughout the mesenchyme, with higher levels overlying areas of future bone and the ventral portion of the neural tube. A strong signal, seen in the same portion of the ventral hindbrain in which signal was previously observed for mTld, is consistent with expression of mTll in the floor plate. A regular pattern of strong expression was observed overlying the connective tissue between the developing vertebra. The high mTll signal observed in the mesenchyma of the developing lung contrasts with the absence, or very low level, of expression in liver which mirrors the relative amounts of mTll mRNA found in adult mouse lung and liver by Northern Blot analysis. In a parasagittal section of a 13.5 day post-coitum embryo, expression was observed in mesenchymal elements of the developing tongue, nasal process, and jaw and in the submucosal layer in loops of the developing intestine. mTll expression was observed overlying a developing atrioventricular valve of the heart.

A major difference between the distribution of mTll and mTld mRNA in developing mouse tissues is seen overlying the neuroepithelium in the vestibular area of the floor of the fourth ventricle of the developing brain where strong mTll expression was consistently observed, in various sections, and where neither mTld nor BMP expression has been observed. mTll RNA expression was observed, in a number of sections, to overlie the neuroepithelial lining of the ventricles and aqueduct of neonatal brain. mTll expression was also observed overlying specific nuclei within the thalamus and the neuroepithelial lining of the lateral ventricles. In adult brain, strong mTll expression was observed in the granular layer of the cerebellum. Weaker mTll expression was also observed overlying other structures of the neonatal and adult mouse brain. Northern blot analysis of RNA from various portions of human brain has also detected relatively strong signal for mTll in the human cerebellum.

Another difference noted between the distribution of mTll mRNA and that previously described for mTld was in a developing spinal cord where mTll expression was more extensive than was previously noted for mTld, extending beyond the floor plate toward more dorsal portions of the spinal cord. In other developing tissues, the distribution of mTll and mTld transcripts appear to overlap.

It is specifically envisioned that equivalents of the mTll gene can be isolated from other species, by probing a cDNA library from cells of an appropriate species with a probe selected to include an mTll-specific portion of the described mouse gene. An mTll-specific portion of the mouse mTll gene can be obtained by comparing the nucleic acid sequence of the mouse mTll coding region to that of BMP-1/mTld and selecting a portion of the mTll gene that has no equivalent in BMP-1. To be an effective probe, the selected sequence should not contain repeat sequences that would cross-hybridize to numerous genomic sites. The probe should be at least about 200 bases long. It is recognized that the genes of the BMP-1 family are most variable in the regions that encode the proregion and the C-terminal 17 amino acids of the proteins, and it is anticipated that suitable probes can be isolated from those regions of the mTll gene. In SEQ ID NO:2, this region corresponds to the sequence shown between about bases 3599 and 3650 for the C-terminal portion and about 701–1051 for the proregion. Such a fragment can be converted into a probe by nick translation, end labeling, or other suitable technique known to the art. It is also understood that a desired fragment (or indeed an entire gene) can be synthesized in vitro using well-known techniques available to the molecular biologist.

This has been accomplished using human source DNA. To obtain human mTll sequences, a 677 bp NdeI-Eco72I fragment of mouse mTll cDNA clone KO 3, corresponding to a portion of CUB4 and all of CUB5 and the carboxy terminus, was used to screen a human placenta genomic DNA library. Genomic clone 151-2 was isolated which contained the final three exons of the human TLL gene. A 339 bp TaqI fragment of mouse mTll cDNA KO 7-2, corresponding to a part of the proregion was then used to screen the same human genomic DNA library resulting in isolation of genomic clones 5-2 and 8, each of which contained the first, 5'-most, exon of the Tll gene. Oligonucleotide primers were synthesized corresponding to sequences in the 5'- and 3'-untranslated regions and were used with cDNA synthesized from human fetal cartilage RNA for long distance PCR amplification of the remainder of TLL coding sequences. The forward primer was 5'-TCTTGCAGTCAGTTGCTTTGCTGG-3' (SEQ ID NO:10). The reverse primer was 5'-TAGTGCGGCCGCACATTCCTTTGTGTTC-3' (SEQ ID NO:11).

The nucleic acid sequence of human mTll is shown in SEQ ID NO:4. The protein encoded by the gene is shown in SEQ ID NO:5. The gene (or portions thereof) can be used in the same ways as the murine gene, but with the additional benefit for genetic therapies, diagnoses, and the like, since there is no need to adapt the gene for use in humans, as could be the case for the mouse mTll gene.

Because defects in mTll may lead to genetic abnormalities in people, the chromosomal position of the human TLL gene was established. A 527 bp cDNA PCR product, corresponding to the last 3 exons of the human TLL gene, was hybridized to Southern blots of EcoRI-digested genomic DNA from panels of human-mouse cell hybrids. Strong hybridization to ~5.1 and 9.5 kb human bands was observed and examination of DNA from 30 hybrid lines, derived from 17 unrelated human cell lines and 4 mouse cells lines (Takahara, K., et al., *J. Biol. Chem.* 269: 26280–26285 (1994)), showed that the segregation of TLL correlated with the distribution of human chromosome 4. Of the cell hybrids examined, one that retained a translocation of human chromosome 4 further localized TLL to the chromosome 4 long arm. Cell hybrid 55R16 has no intact chromosome 4 but retains the 11/4 translocation 11qter-11p13::4q25-4qter. These results localized TLL to the 4q25-4qter region. The TLL gene was independently mapped by fluorescence in situ hybridization (FISH) on human metaphase chromosome spreads by the method of Trask, B., *Methods Cell Biol.* 35: 1–35 (1992). Human genomic DNA clone 8, which contains the TLL first exon and has an insert size of approximately 16 kb, was labeled with digoxygenin-11-dUTP (Boehringer Mannheim) by random priming (Feinberg, A. P., and B. Vogelstein, B. *Anal. Biochem.* 132: 6–13 (1983)) and employed as a probe for FISH analysis. Images were obtained and analyzed as described (Takahara, K., et al., supra). Double fluorescent signals were found only at 4q32-4q33 in 16/18 of the metaphase spreads examined (88.8%), with double fluorescent signals found on both chromosomes of 10/18 metaphase spreads and on no other chromosome, localizing TLL to this region.

It should also be possible to use PCR to amplify a portion of a genome that corresponds to the mTll region, by selecting specific primers expected to flank the mTll gene (or any portion of the gene). Two mTll-specific portions of the gene can serve as suitable primers. It may not be effective to select primers outside the coding portion of the gene because reduced selective pressure on non-coding portions results in greater divergence between mice and other species in those regions. It is specifically noted that the genes of the BMP family from humans and model species such as the mouse are particularly sought after for their relation to human deformities (see, e.g., "The Chicken With a Duck's Feet: It's All in the Biochemical Signal," *The New York Times*, National Edition, p. B6 (May 21, 1996)).

It is also specifically envisioned that large quantities of the protein encoded by the mTll gene can be expressed in (or secreted from) host cells, purified to a substantially pure preparation and used in subsequent functional assays. In one such functional assay, functional attributes of the expressed protein will be described. The protein functions are expected to include a metalloprotease activity, C-proteinase activity and laminin-5 processing activity, and an activating activity for TGF-β-like proteins, such predictions being reasonable in view of the gross structural similarity to known proteins at the domain level.

In another assay, the protein can be used to screen putative agents having inhibitory activity against the protein. Given that mTll is able to rescue BMP-1 knockout mice, it will be important for any therapeutic system that modifies or eliminates BMP-1 protein function to similarly alter the mTll protein function. Thus, any panel of such agents must be screened against mTll protein. In such an assay, all components of an assay that support mTll function can be added together, under suitable conditions of salt and pH, and combined with a panel of putative inhibitors of protein function. Using established assays of protein function (described in documents incorporated elsewhere herein by reference), it will be possible to determine whether any tested agent can inhibit protein activity, thereby making it a likely candidate for use in a therapeutic amount to inhibit fibrosis, reduce scarring, and reduce keloids. Such screening efforts are underway using related proteins from the BMP-1 family of genes. See Kessler, supra.

It is now also possible to embark upon a rational drug design strategy using the disclosed protein or fragments thereof. In doing so, the protein or fragments will be subjected to x-ray crystallographic analysis to determine their active sites and sites that are available for interaction with a putative therapeutic agent.

The protein encoded by BMP-1 was recently shown to cleave procollagen near the C-terminus. This C-proteinase activity, which is essential to the production of collagen, had long been thought to reside in a protein that had remained elusive. There is great commercial interest in harnessing the C-proteinase activity as a therapeutic agent in collagen-related diseases. Since mTll appears to be the only other mammalian gene closely related to BMP-1 (on the basis of the cDNA library screening results), it is also specifically contemplated that the protein encoded by mTll will be an alternative C-proteinase and, further, that the mTll gene can be utilized in the effort to produce an alternative C-proteinase, both by incorporating the gene into a recombinant vector for ex vivo production of therapeutic protein, and for direct administration in a genetic therapy. The human gene has particular utility for these applications.

The invention will be better understood upon consideration of the following non-limiting Examples.

EXAMPLES

BMP-1/mTld-null Mouse Embryo cDNA Library

Mouse embryo fibroblasts (MEFs) were prepared as described (Hogan et al., "Manipulating the Mouse Embryo: A Laboratory Manual, 2nd Ed.," pp. 260–261, Cold Spring Harbor Laboratory, Cold Spring Harbor, N.Y. (1994)). Ten 150 mm plates of MEFs prepared from embryos made homozygous for null alleles of the BMP-1/mTld gene (express no BMP-1/mTld proteins) were grown to confluence (in DMEM, 10% fetal calf serum), and 3 days later were treated with 50 µg/ml ascorbate for 18 hr, harvested, and 42 µg poly($A^+$) mRNA was isolated using a FastTrack kit (Invitrogen). A 5 µg aliquot of poly($A^+$) was then used for synthesis of double-stranded cDNA with EcoRI ends using the SuperScript Choice System (Gibco-BRL). This cDNA was then ligated to EcoRI-cut λgt10 arms and packaged using Gigapak II Gold packaging extract (Stratagene). The 5 µg of poly ($A^+$) provided an unamplified library of ~2.2×10$^6$ PFUs. The randomly picked clones had an average insert size of ~2.9 kb.

DNA Sequence Analysis

Restriction fragments were subcloned into pBluescript II KS$^+$ and sequences were obtained from double-stranded templates by dideoxy chain termination, as described in Lee S.-T., et al., "Construction of a full-length cDNA encoding human pro-alpha 2(I) collagen and its expression in pro-alpha 2(I)-deficient W8 rat cells," *J. Biol. Chem.* 263:13414–13418 (1988). Ends of subclones were sequenced using T3 and T7 primers with internal portions of subclones made accessible to sequencing by introducing deletions or using primers complementary to insert sequences. The mTll sequences reported herein were confirmed by sequencing both strands.

Polymerase Chain Reaction (PCR)

The PCR was performed with 0.2 µM of each primer in a 480 thermal cycler (Perkin-Elmer Corp.) with denaturation at 94° C. for 3 min, followed by 35 cycles of 94° C./1 min, 57° C./1 min, 72° C./1.5 min, and final incubation at 72° C./8 min. Final volumes were 100 µl of 10 mM Tris-HCL, pH 8.3, 50 mM KCL, 1.5 mM MgCl$_2$, 0.01% (w/v) gelatin, 0.2 mM each DNTP, and 2.5 units of Taq polymerase (Perkin-Elmer Corp.).

Tissue Sections for in situ Hybridization

Tissue sections mounted on slides for in situ hybridization were kindly provided by G. E. Lyons (University of Wisconsin-Madison). Mouse tissues were fixed and embedded, as in Lyons et al., "The expression of myosin genes in developing skeletal muscle," *J. Cell Biol.* 111:1465–1476 (1990). Briefly, tissues were fixed in 4% paraformaldehyde in phosphate-buffered saline, dehydrated, and infiltrated with paraffin. Serial sections, 5–7 µm thick, were mounted on gelatinized slides. One to three sections were mounted/slide, deparaffinized in xylene, and rehydrated. Sections were digested with proteinase K, post-fixed, treated with tri-ethanolamine/acetic anhydride, washed, and dehydrated.

Probes for in Situ Hybridization mTll-specific probes corresponding to portions of the 1104 bp mTll 3'-untranslated region were used for in situ hybridization. Since the 3'-untranslated region has no similarity to BMP-1 or mTld sequences, the probes did not cross-hybridize with BMP-1 or mTld RNA.

To ensure that the probes did not hybridize to other RNA transcripts bearing repeat sequences similar to the long SSR identified in the central portion of the mTll 3'-untranslated region (nucleotides 4148 to 4239), two separate riboprobes, corresponding to 3'-UT sequences upstream or downstream of the SSR were prepared according to the manufacturer's conditions (Stratagene), labeled with $^{35}$S-UTP (>1000 Ci/mmol/Amersham Corp.) and combined to strengthen the in situ hybridization signal. Probes were hydrolyzed with alkali to a mean size of 70 bases.

For 3'-untranslated sequences downstream of the SSR, a 399 bp PCR product (SEQ ID NO:2 nucleotides 4283 to 4681) was prepared using forward primer 5'-CCAGCTTAACCTGTTCACAC-3' (SEQ ID NO:6) and reverse primer 5'-AACTCTACTTCCACTTCATC-3' (SEQ ID NO:7). The PCR product was ligated into the cloning site of the pCRII T-A vector (Invitrogen). Uniformly labeled antisense riboprobe was generated by linearizing the template at the HindIII site in the pCRII polylinker and transcribing with RNA polymerase T7. Sense control riboprobe was generated by linearizing at the XhoI site in the pCRII polylinker and transcribing with RNA polymerase SP6.

For 3'-untranslated sequences upstream of the SSR, a 420 bp PCR product (SEQ ID NO:2, nucleotides 3666 to 4085) was prepared, employing forward primer 5'-TCAGAACAGAAAGGAATGTG-3' (SEQ ID NO:8) and reverse primer 5'-GACCACTATTCCACATCACC-3' (SEQ ID NO:9), and was ligated into the cloning site of PCRII T-A. Antisense riboprobe was prepared by linearizing at the XhoI site in the pCRII polylinker and transcribing with RNA polymerase SP6, while sense control riboprobe was prepared by linearizing at the HindIII site in the pCRII polylinker and transcribing with RNA polymerase T7.

In situ hybridization and Washing Procedures

Sections were hybridized overnight at 52° C. in 50% deionized formamide, 0.3 M NaCl, 20 mM Tris-HCl, pH 7.4, 5 mM EDTA, 10 mM NaPO$_4$, 10% dextran sulfate, 1×Denhardt's solution, 50 µg/ml total yeast RNA, 25 µmol/ml thio-ATP (Boehringer-Mannheim), and 50–75,000 cpm/µl $^{35}$S-labeled cRNA probe. Tissue was stringently washed at 65° C. in 50% formamide, 2×SSC, 10 mM dithiothreitol; rinsed in phosphate-buffered saline; and treated with 20 µg/ml RNase A at 37° C. for 30 min. Following washes in 2×SSC and 0.1×SSC for 15 min at 37° C., slides were dehydrated, dipped in Kodak NTB-2 nuclear track emulsion, and exposed for 1 week in light-tight boxes with desiccant at 4° C. Photographic development was in Kodak D-19.

Slides were analyzed using light- and dark-field optics of a Zeiss Axiophot microscope.

Northern and Southern Blot Analyses

A 1,633 bp EcoRI fragment (SEQ ID NO:2, nucleotides 1113 to 2745) corresponding to the 5'-end of cDNA clone KO 3 (FIG. 1) was purified and used as a probe for Northern blot analyses. This fragment contains sequences corresponding to most of the protease domain; all of the domains CUB1, CUB2 and EGF1; and most of domain CUB3. The 399 bp PCR product described above for use in in situ hybridization experiments was gel purified and used as a probe in Southern blot analyses. Both probes were radiolabeled to a specific activity of $4-6 \times 10^9$ cpm/µg by random priming (Feinberg and Vogelstein, "A technique for radiolabeling DNA restriction endonuclease fragments to high specific activity: Addendum," *Anal. Biochem.* 137:266–267 (1984)) and were hybridized to blots in QuickHyb (Stratagene) at 68° C. for 1 h. Northern blots (obtained from Clontech) were washed twice in 2×SSC, 0.1% SDS at 68° C. for 10 min and then twice in 0.1×SSC, 0.1% SDS at 68° C. for 15 min. Southern blots were washed twice in 2×SSC, 0.1% SDS at 68° C. for 10 min and then twice in 0.1×SSC, 0.1% SDS at 68° C. for 20 min.

Subcloning and expression of mTll gene

The mature active forms of BMP-1, mTld and mTll are all similar in their amino acid sequences. An exception to this is the C-terminus of each protein, where no homology is observed. This uniqueness of C-terminal sequences has been put to use in producing a set of polyclonal antibodies capable of discriminating between the three protein forms. In the case of mouse mTll, the synthetic peptide Ac-CYIRYKSIRYPETMHAKN-OH (residues 997 to 1013 of SEQ ID NO:3), which corresponds to the final 17 amino acids of mTll, was linked to the protein carrier Keyhole Limpet Hemocyanin, suspended in saline and emulsified by mixing with an equal volume of Freund's adjuvant and injected into three to four subcutaneous dorsal sites in each of two rabbits. Bleeds for sera were at 12 and 16 weeks after immunization and boosts. Unlike BMP-1 and mTld, for which C-terminal amino acid sequences are perfectly conserved between mouse and human, mouse and human mTll C-terminal amino acid sequences are diverged. It is perhaps because of this divergence across species that the peptide for the mouse mTll C-terminus peptide has produced 3-fold higher titers of antibodies in rabbits than have the C-terminus peptides of BMP-1 and mTld. In order to produce antibodies specific for the C-terminus of human MTll, the peptide Ac-CHIRYKSIRYPDTTHTKK-OH (residues 997 to 1013 of SEQ ID NO:3), will be used. These antibodies have commercial utility in an assay for visualizing the production and localization of mTll protein in cells, tissues, and mammalian organisms, including, but not limited to model systems (e.g., rodents, primates, and the like) as well as humans. In view of the rapid pace at which the understanding of the bone morphogenetic proteins is advancing, the ability to distinguish individual components one from another is important, not merely from a research perspective, but in monitoring the level and distribution of BMP system components in patients having disorders of the BMP system. Such disorders could include, for example, in mice and humans, fibrotic conditions. In addition, hereditary developmental abnormalities may be due to defects in the TLL gene. Determining the role of mTll in such genetic abnormalities will be enabled by the antibody and nucleic acid probes described herein. The mTll protein is quite clearly important in the BMP system, in that it apparently substitutes well for BMP-1 in mice having null BMP-1 alleles on both chromosomes. Such mice survive the full course of gestation but develop a persistent herniation of the gut in the umbilical region. These mice die soon after birth, presumably due to the loss of the BMP-1/mTld gene. However, they show no gross derangements of pattern formation, of collagen fibril formation, or of development in general. Clearly development of this order or even collagen fibrillogenesis would not be possible without some BMP-1/mTld-like activity. We have found such an activity in mouse embryo fibroblasts from these BMP-1-null mice in the form of C-proteinase activity. Such activity appears to be supplied by mTll and there appear to be no other closely related genes.

We claim:

1. An isolated polynucleotide that encodes an amino acid sequence selected from the group consisting of YIRYKSIRYPETMHAKN (amino acid residues 997 to 1013 of SEQ ID NO:3), HIRYKSIRYPDTTHTKK (amino acid residues 997 to 1013 of SEQ ID NO:5), the amino acid sequence of SEQ ID NO:3 between amino acids 31 and 147, and the amino acid sequence of SEQ ID NO:5 between amino acids 31 and 147.

2. A genetic construct comprising in 5' to 3' order:

a transcriptional promoter active in a host cell; and a polynucleotide that encodes an amino acid sequence selected from the group consisting of YIRYKSIRYPETMHAKN (amino acid residues 997 to 1013 of SEQ ID NO:3), HIRYKSIRYPDTTHTKK (amino acid residues 997 to 1013 of SEQ ID NO:5), the amino acid sequence of SEQ ID NO:3 between amino acids 31 and 147, and the amino acid sequence of SEQ ID NO:5 between amino acids 31 and 147.

3. An isolated polynucleotide as claimed in claim 1 comprising the nucleotide sequence of SEQ ID NO:2 between nucleotides 3599 and 3650.

4. An isolated polynucleotide as claimed in claim 1 comprising the nucleotide sequence of SEQ ID NO:4 between nucleotides 3636 and 3686.

5. An isolated polynucleotide as claimed in claim 1 comprising the nucleotide sequence of SEQ ID NO:2 between nucleotides 701 and 1051.

6. An isolated polynucleotide as claimed in claim 1 comprising the nucleotide sequence of SEQ ID NO:4 between nucleotides 738 and 1088.

7. An isolated polynucleotide as claimed in claim 1, the polynucleotide encoding a polypeptide that comprises a pair of amino acid sequences selected from the group consisting of (1) YIRYKSIRYPETMHAKN (amino acid residues 997 to 1013 of SEQ ID NO:3) and the amino acid sequence of SEQ ID NO:3 between amino acids 31 and 147 and (2) HIRYKSIRYPDTTHTKK (amino acid residues 997 to 1013 of SEQ ID NO:5) and the amino acid sequence of SEQ ID NO:5 between amino acids 31 and 147.

8. An isolated polynucleotide as claimed in claim 7, the polynucleotide comprising the nucleotide sequence of SEQ ID NO:2 between nucleotides 3599 and 3650.

9. An isolated polynucleotide as claimed in claim 7, the polynucleotide comprising the nucleotide sequence of SEQ ID NO:2 between nucleotides 701 and 1051.

10. A genetic construct as claimed in claim 2 wherein the polynucleotide fragment comprises a nucleotide sequence selected from the group consisting the nucleotide sequence of SEQ ID NO:2 between nucleotides 701 and 1051, the nucleotide sequence of SEQ ID NO:2 between nucleotides 3599 and 3650, the nucleotide sequence of SEQ ID NO:4 between nucleotides 738 and 1088, and the nucleotide sequence of SEQ ID NO:4 between nucleotides 3636 and 3686.

11. A genetic construct as claimed in claim 2, the polynucleotide encoding a polypeptide that comprises a pair of amino acid sequences selected from the group consisting of (1) YIRYKSIRYPETMHAKN (amino acid residues 997 to 1013 of SEQ ID NO:3) and the amino acid sequence of SEQ ID NO:3 between amino acids 31 and 147 and (2) HIRYKSIRYPDTTHTKK (amino acid residues 997 to 1013 of SEQ ID NO:5) and the amino acid sequence of SEQ ID NO:5 between amino acids 31 and 147.

12. A genetic construct as claimed in claim 11, the polynucleotide comprising the nucleotide sequence of SEQ ID NO:2 between nucleotides 3599 and 3650.

13. A genetic construct as claimed in claim 11, the polynucleotide comprising the nucleotide sequence of SEQ ID NO:2 between nucleotides 701 and 1051.

14. A genetic construct as claimed in claim 11, the polynucleotide comprising the nucleotide sequence of SEQ ID NO:4 between nucleotides 3636 and 3686.

15. A gentic construct as claimed in claim 11, the polynucleotide comprising the nucleotide sequence of SEQ ID NO:4 between nucleotides 738 and 1088.

16. An isolated polynucleotide that encodes a protein comprising an amino acid sequence selected from the group consisting of SEQ ID NO:3 and SEQ ID NO:5.

17. A method for delivering generic material into a suitable host cell in vitro, the method comprising the step of:
    administering into the host cell an isolated polynucleotide as claimed in claim 1.

18. An isolated cell comprising the genetic construct of claim 2.

* * * * *

UNITED STATES PATENT AND TRADEMARK OFFICE
CERTIFICATE OF CORRECTION

PATENT NO. : 5,939,321
DATED : August 17, 1999
INVENTOR(S) : Daniel S. Greenspan, et al.

It is certified that error appears in the above-identified patent and that said Letters Patent is hereby corrected as shown below:

Column 1, line 5,

--This invention was made with United States Government Support awarded by the following agency: NIH Grant #: GM46846. The United States government has certain rights in this invention.--

Signed and Sealed this

First Day of February, 2000

Attest:

Attesting Officer

Q. TODD DICKINSON

Acting Commissioner of Patents and Trademarks